(12) United States Patent
Goto et al.

(10) Patent No.: US 9,932,522 B2
(45) Date of Patent: Apr. 3, 2018

(54) ELECTROCHROMIC COMPOUND, ELECTROCHROMIC COMPOSITION, DISPLAY ELEMENT, AND DIMMING ELEMENT

(71) Applicants: Daisuke Goto, Kanagawa (JP); Toshiya Sagisaka, Kanagawa (JP); Shigenobu Hirano, Kanagawa (JP); Satoshi Yamamoto, Kanagawa (JP); Mamiko Inoue, Tokyo (JP); Tohru Yashiro, Kanagawa (JP); Hiroyuki Takahashi, Kanagawa (JP); Koh Fujimura, Tokyo (JP); Tamotsu Horiuchi, Shizuoka (JP); Keiichiroh Yutani, Kanagawa (JP); Yoshihisa Naijo, Kanagawa (JP); Yoshinori Okada, Kanagawa (JP); Kazuaki Tsuji, Kanagawa (JP); Sukchan Kim, Kanagawa (JP); Keigo Takauji, Kanagawa (JP)

(72) Inventors: Daisuke Goto, Kanagawa (JP); Toshiya Sagisaka, Kanagawa (JP); Shigenobu Hirano, Kanagawa (JP); Satoshi Yamamoto, Kanagawa (JP); Mamiko Inoue, Tokyo (JP); Tohru Yashiro, Kanagawa (JP); Hiroyuki Takahashi, Kanagawa (JP); Koh Fujimura, Tokyo (JP); Tamotsu Horiuchi, Shizuoka (JP); Keiichiroh Yutani, Kanagawa (JP); Yoshihisa Naijo, Kanagawa (JP); Yoshinori Okada, Kanagawa (JP); Kazuaki Tsuji, Kanagawa (JP); Sukchan Kim, Kanagawa (JP); Keigo Takauji, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/315,103

(22) PCT Filed: Jun. 17, 2015

(86) PCT No.: PCT/JP2015/003028
§ 371 (c)(1),
(2) Date: Nov. 30, 2016

(87) PCT Pub. No.: WO2016/002151
PCT Pub. Date: Jan. 7, 2016

(65) Prior Publication Data
US 2017/0226413 A1    Aug. 10, 2017

(30) Foreign Application Priority Data

Jul. 3, 2014 (JP) .................. 2014-137423
Apr. 21, 2015 (JP) .................. 2015-086433

(51) Int. Cl.
*C09K 9/02* (2006.01)
*C07F 9/38* (2006.01)
(Continued)

(52) U.S. Cl.
CPC .............. *C09K 9/02* (2013.01); *C07F 9/3808* (2013.01); *C09B 57/00* (2013.01); *G02F 1/15* (2013.01);
(Continued)

(58) Field of Classification Search
CPC .............. C09K 9/02; C09K 2211/1018; C09K 2211/1007; C09K 2211/1037;
(Continued)

(56) References Cited

U.S. PATENT DOCUMENTS 7,166,689 B2    1/2007  Sagisaka et al.
7,446,923 B2 *  11/2008 Ishii .................. G02F 1/15
                                                136/244
(Continued)

FOREIGN PATENT DOCUMENTS

JP    2006-267829    10/2006
JP    2011-085773    4/2011
(Continued)

OTHER PUBLICATIONS

International Search Report dated Sep. 29, 2015 for counterpart International Patent Application No. PCT/JP2015/003028 filed Jun. 17, 2015.

*Primary Examiner* — Loha Ben
(74) *Attorney, Agent, or Firm* — Oblon, McClelland, Maier & Neustadt, L.L.P.

(57) ABSTRACT

To provide an electrochromic compound, represented by the following general formula (I), where $Ar_1$ is a pyridinium ring
(Continued)

having a structure represented by the following general formula (IIa), (IIb), or (IIc), where $Ar_2$ is a monovalent heterocyclic ring which may have a substituent, but $Ar_2$ is not a pyridinium ring; $R_1$ to $R_8$ are each independently a monovalent group which may have a functional group, where the monovalent group may have a substituent; A is a monovalent group which may have a functional group, where the monovalent group may have a substituent; and $B^-$ is a monovalent anion.

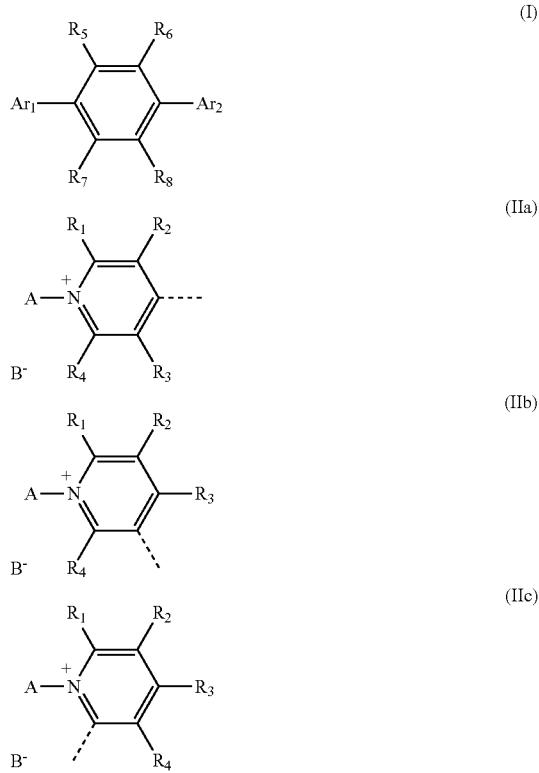

12 Claims, 6 Drawing Sheets

(51) Int. Cl.
   *C09B 57/00* (2006.01)
   *G02F 1/15* (2006.01)
   *G02F 1/155* (2006.01)
   *G02F 1/153* (2006.01)
   *G02F 1/01* (2006.01)

(52) U.S. Cl.
   CPC .............. *G02F 1/153* (2013.01); *G02F 1/155* (2013.01); *C09K 2211/1007* (2013.01); *C09K 2211/1037* (2013.01); *C09K 2211/1051* (2013.01); *C09K 2211/1059* (2013.01); *C09K 2211/1074* (2013.01); *G02F 1/01* (2013.01); *G02F 2001/1555* (2013.01)

(58) Field of Classification Search
   CPC .... C09K 2211/1051; C09K 2211/1059; C09K 2211/1074; C09K 2211/1441; C07F 9/38; C07F 9/3808; C09B 57/00; C09B 62/02; G02F 1/01; G02F 1/0018; G02F 1/15; G02F 1/1525; G02F 1/153; G02F 1/155; G02F 2001/1555; G02F 2001/1552; C07D 213/38; C07D 213/57
   USPC ......... 359/265–275; 252/502, 510, 582, 586, 252/589
   See application file for complete search history.

(56) References Cited

U.S. PATENT DOCUMENTS

| | | | |
|---|---|---|---|
| 7,816,674 B2 | 10/2010 | Kato et al. | |
| 8,440,713 B2 | 5/2013 | Goto et al. | |
| 8,593,715 B2 * | 11/2013 | Yashiro | C07D 213/38 359/273 |
| 8,680,296 B2 | 3/2014 | Goto et al. | |
| 8,687,262 B2 * | 4/2014 | Yashiro | G02F 1/1525 359/265 |
| 2007/0092760 A1 | 4/2007 | Sagisaka et al. | |
| 2009/0230386 A1 | 9/2009 | Yamamoto et al. | |
| 2010/0219405 A1 | 9/2010 | Sagisaka et al. | |
| 2012/0119195 A1 | 5/2012 | Sagisaka et al. | |
| 2012/0139825 A1 | 6/2012 | Yashiro et al. | |
| 2012/0194894 A1 | 8/2012 | Yashiro et al. | |
| 2013/0225858 A1 | 8/2013 | Goto et al. | |
| 2014/0175416 A1 | 6/2014 | Goto et al. | |
| 2014/0187797 A1 | 7/2014 | Goto et al. | |
| 2014/0299877 A1 | 10/2014 | Nakamura et al. | |
| 2015/0001531 A1 | 1/2015 | Ueda et al. | |
| 2015/0028334 A1 | 1/2015 | Matsumoto et al. | |
| 2015/0153624 A1 | 6/2015 | Yamada et al. | |

FOREIGN PATENT DOCUMENTS

| | | |
|---|---|---|
| JP | 2011-102287 | 5/2011 |
| JP | 2011-102382 | 5/2011 |
| JP | 4816069 | 9/2011 |
| JP | 2012-137737 | 7/2012 |
| JP | 2012-224548 | 11/2012 |
| JP | 2015-027987 | 2/2015 |
| WO | WO2014/208775 A1 | 12/2014 |

* cited by examiner

[Fig. 1]
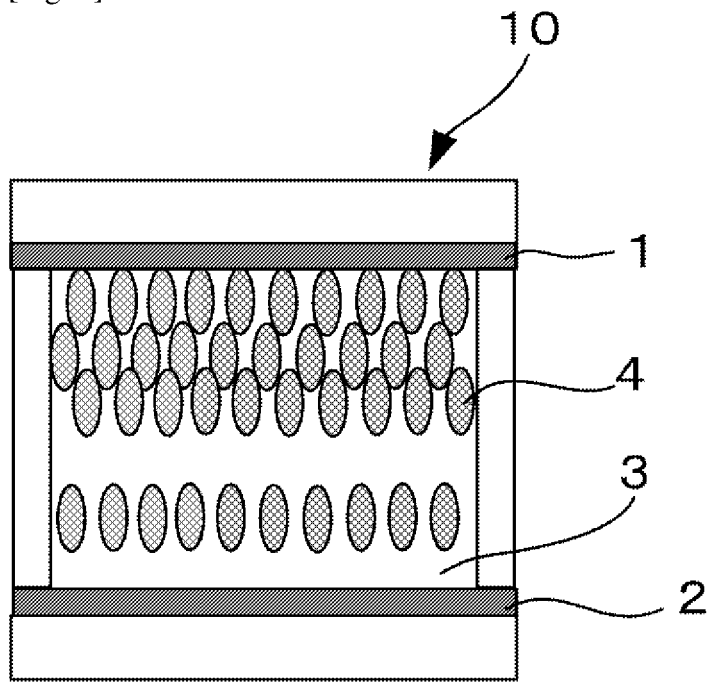
[Fig. 2]
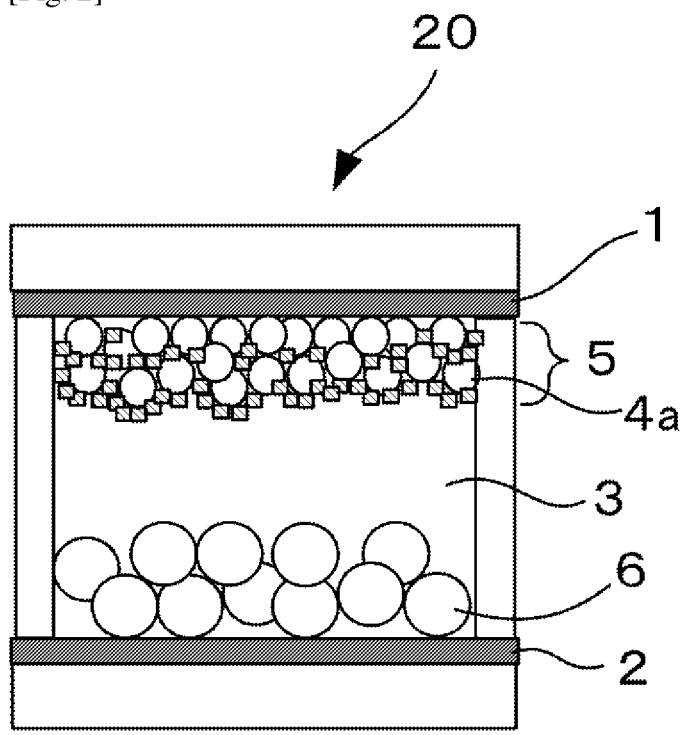

[Fig. 3]
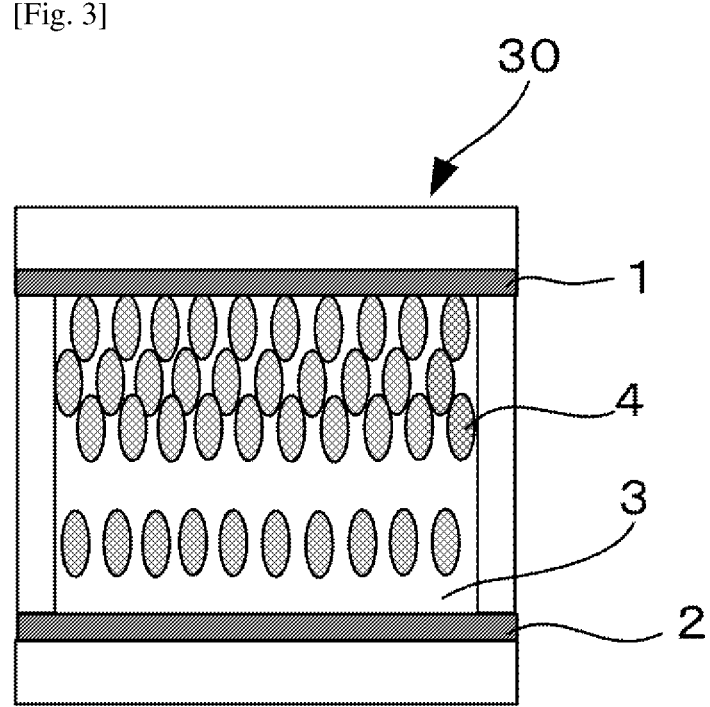
[Fig. 4]
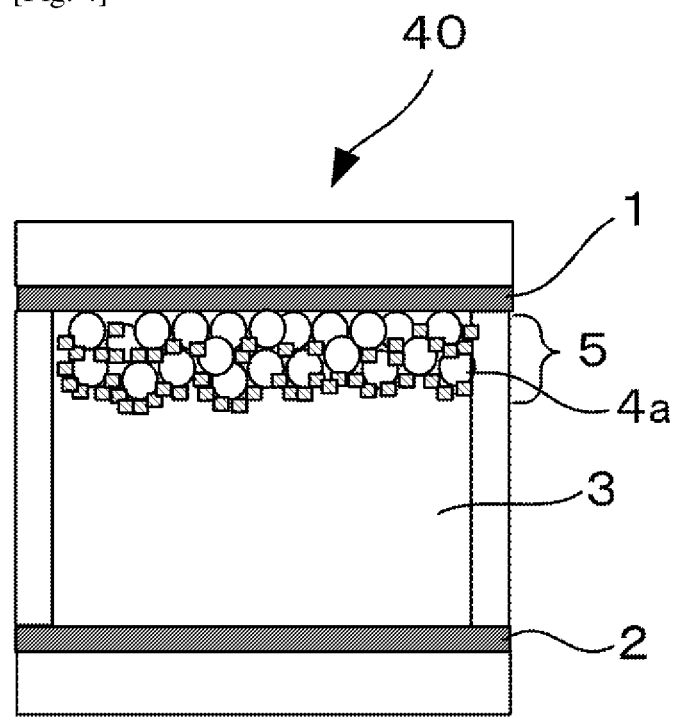

[Fig. 5]
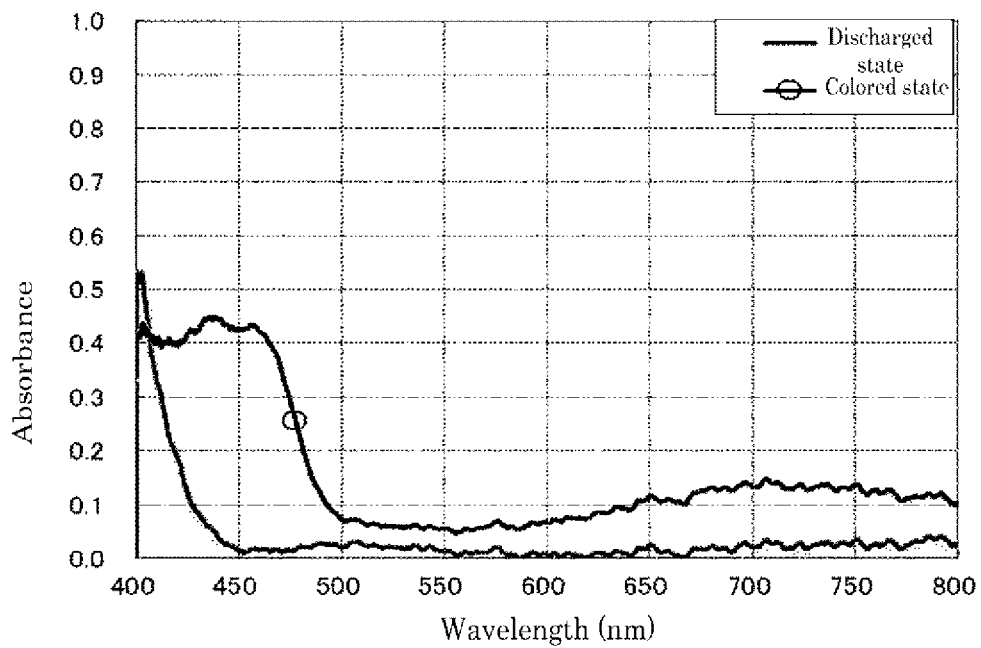
[Fig. 6]
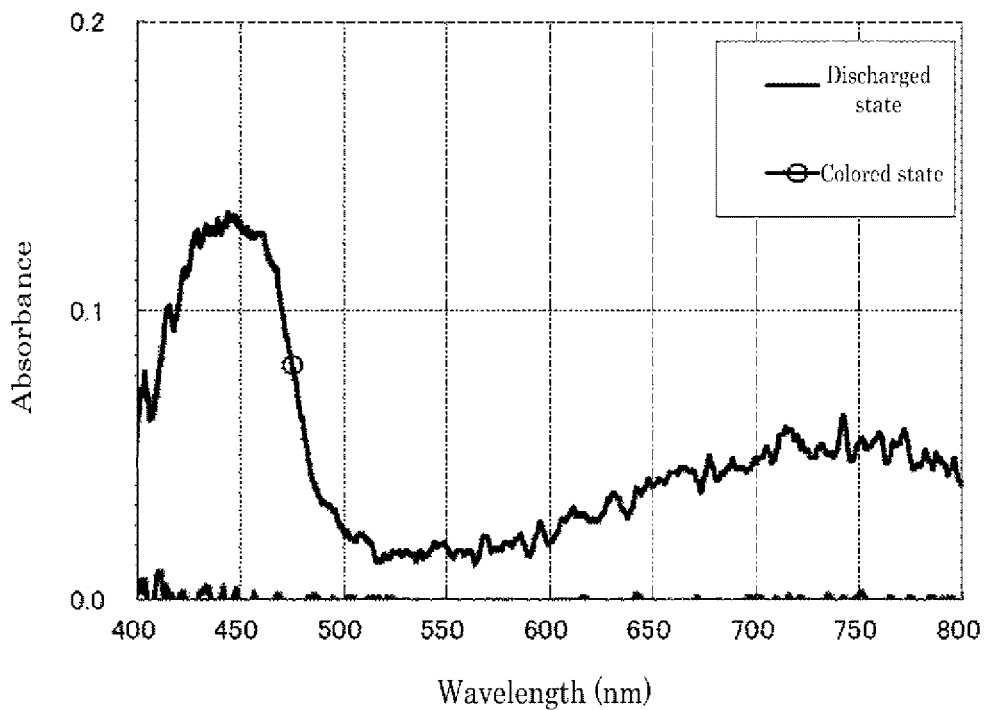

[Fig. 7]
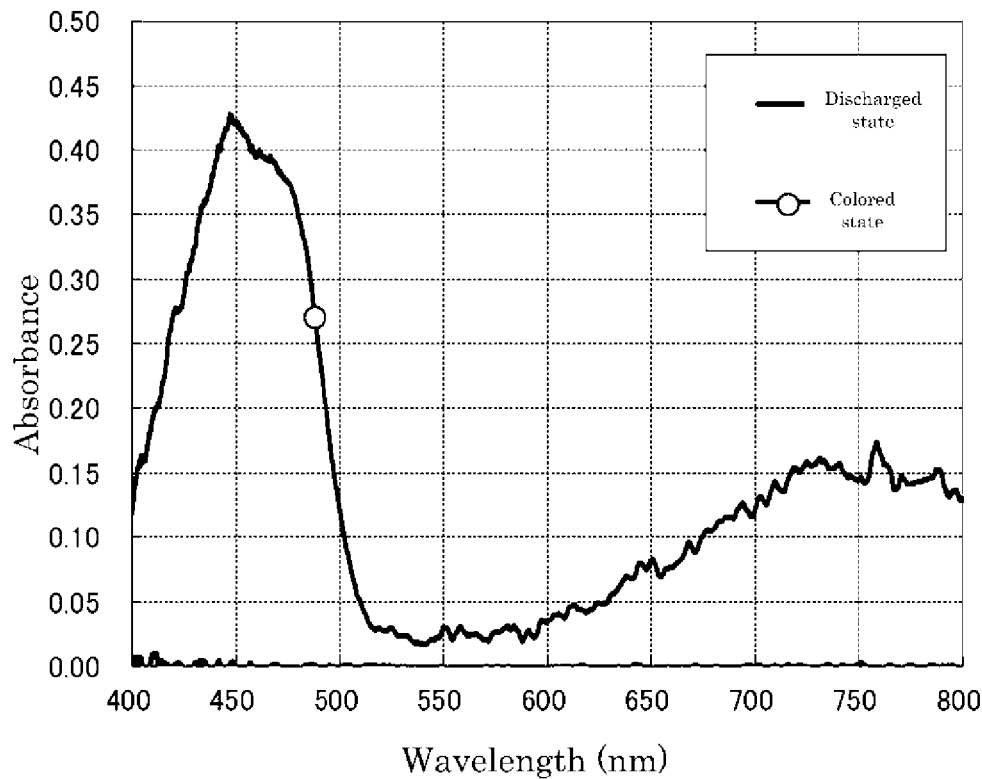
[Fig. 8]
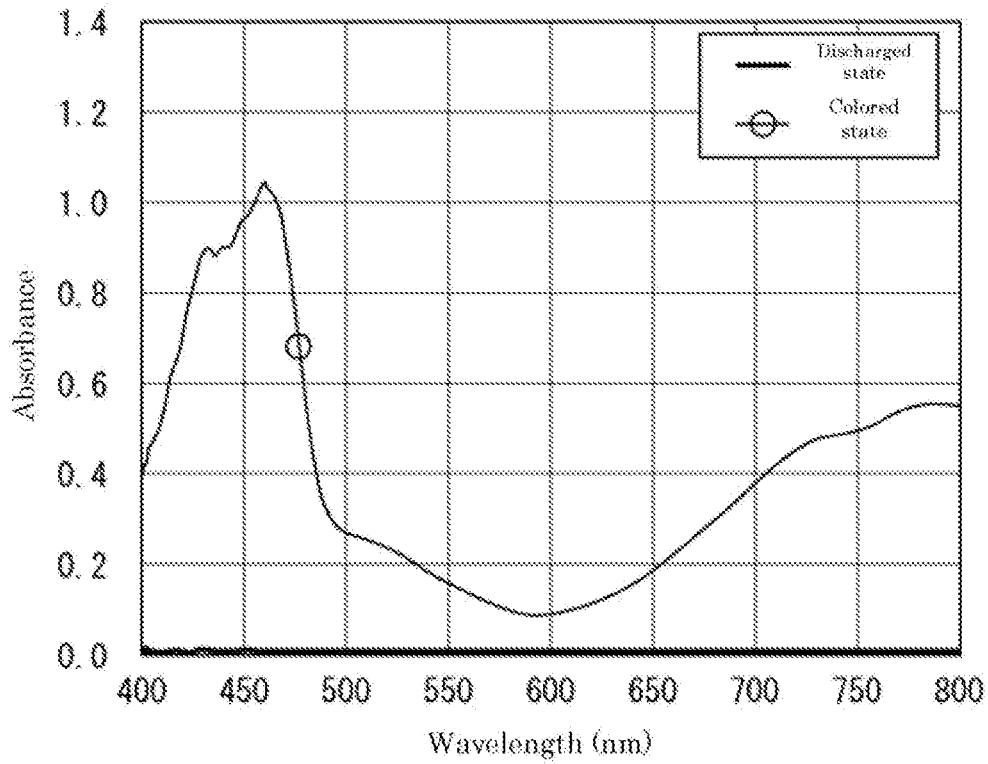

[Fig. 9]
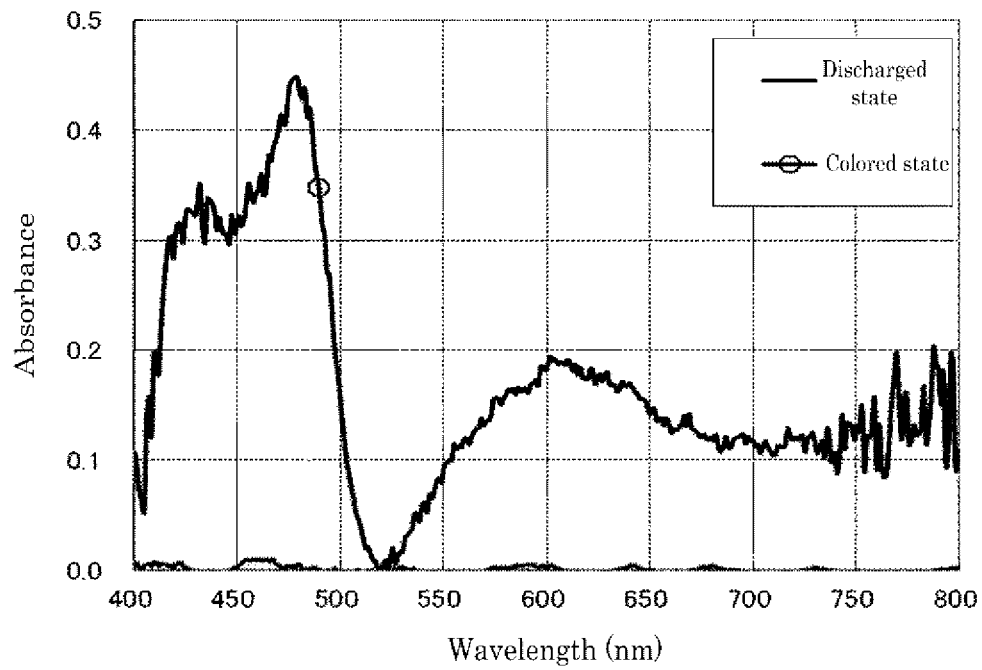
[Fig. 10]
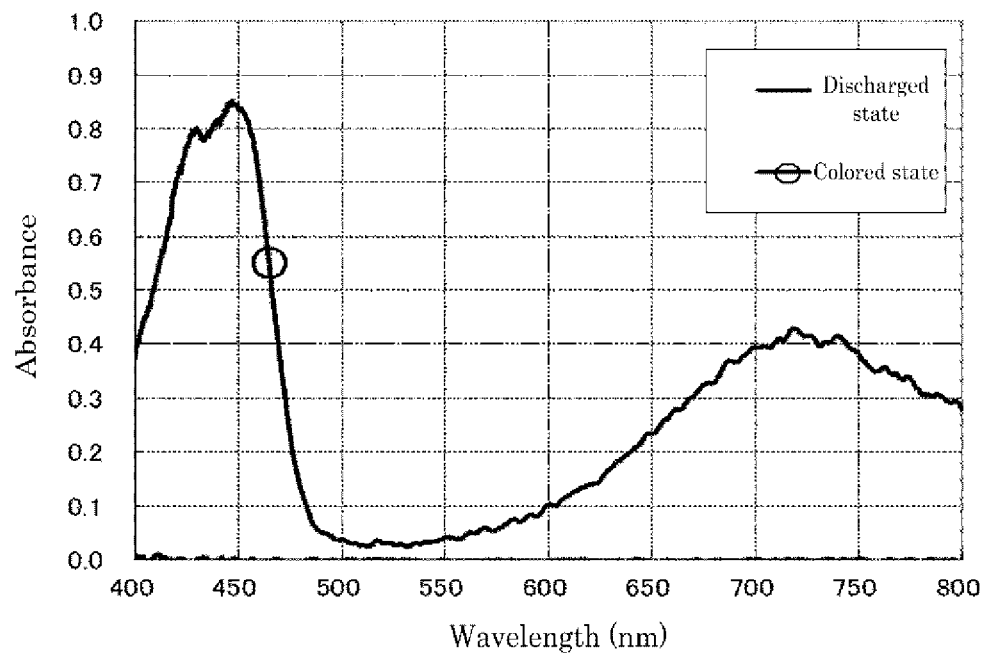

[Fig. 11A]
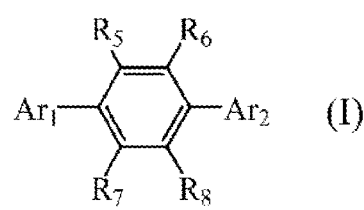
(I)
[Fig. 11B]
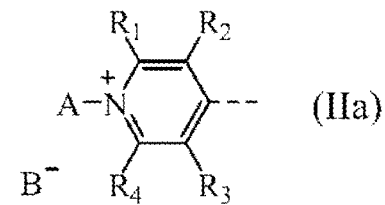
(IIa)
[Fig. 11C]
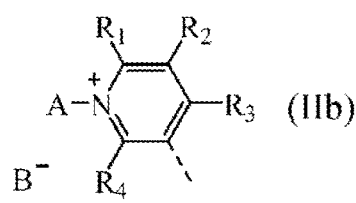
(IIb)
[Fig. 11D]
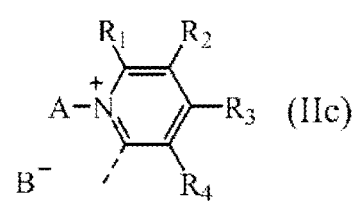
(IIc)

ELECTROCHROMIC COMPOUND, ELECTROCHROMIC COMPOSITION, DISPLAY ELEMENT, AND DIMMING ELEMENT

TECHNICAL FIELD

The present invention relates to an electrochromic compound, an electrochromic composition, and a display element and a dimming element using the electrochromic compound or the electrochromic composition.

BACKGROUND ART

Recently, developments of electronic paper have been actively performed, as the electronic paper is expected to be an electronic media that replace paper. The electronic paper has a characteristic that a display device is used as if it is paper. Therefore, the electronic paper requires different properties from those of conventional display devices, such as CRT, and a liquid crystal display. For example, the required properties for the electronic paper include being a reflective display device, having high white reflectance and a high contrast ratio, realizing highly precise display, giving a memory effect to a display, realizing low voltage drive, being thin and light, and being inexpensive. As for the properties associated with a quality of a display, white reflectance and a contrast ratio similar to those of paper are highly demanded among the aforementioned properties.

As for a display device for use as an electronic paper, for example, devices of a system using reflective liquid crystals, a system using electrophoresis, or a system using toner migration have been proposed. Among them, the electrophoresis system is a mainstream, and is widely used in electronic paper available on the market as commercial products. However, it is particularly difficult to realize high white reflectance with this method. It has been known that the white reflectance realized in this method is a low value, i.e., about 40%, whereas the white reflectance of paper is 80%, and the white reflectance of newspaper is 60%. Therefore, to realize high white reflectance is a large problem in this system.

As for a promising technique for solving the aforementioned problem, and realizing a reflective display device, there is a system using electrochromic phenomenon. The phenomenon where an oxidation-reduction reaction is reversibly caused to reversibly change a color, as voltage is applied, is called electrochromism. A display device utilizing coloring/discharging (referred as to coloring-discharging, hereinafter) of an electrochromic compound that causes this electrochromic phenomenon is an electrochromic display device. The electrochromic display device is a reflective display device, has a memory effect, and can be driven at low voltage. Therefore, researches and developments of the electrochromic display device have been widely conducted from a development of materials to designing of a device, as a strong candidate for a display device technology for use in electronic paper. For example, it has been confirmed in PTL 1 that white reflectance of an electrochromic display device is 60%, which is substantially the same value to that of paper.

Moreover, the electrochromic display device is a system that can solve most of the aforementioned problems. Since conventional materials for use have symmetric structures, and are disubstituted compounds, however, most of the materials have poor solubility due to a quaternary salt structure, and a phosphoric acid group. In addition, it is difficult to purify the materials to a high degree with a simple operation (see PTL 2 to 3).

CITATION LIST

Patent Literature

PTL 1: Japanese Patent Application Laid-Open (JP-A) No. 2006-267829
PTL 2: JP-A No. 2011-102287
PTL 3: Japanese Patent (JP-B) No. 4816069

SUMMARY OF INVENTION

Technical Problem

The present invention aims to provide an electrochromic compound, which has excellent solubility, can be easily highly purified through purification, and is colorless in a discharged state without having an absorption band, when discharged.

Solution to Problem

As means for solving the aforementioned problems, the electrochromic compound of the present invention is represented by the following general formula (I):

[Chem. 1]

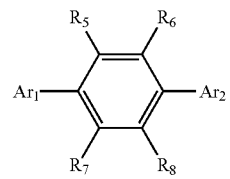

(I)

where $Ar_1$ is a pyridinium ring having a structure represented by the following general formula (IIa), (IIb), or (IIc):

[Chem. 2]

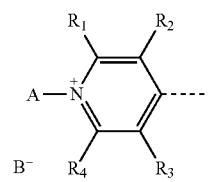

(IIa)

[Chem. 3]

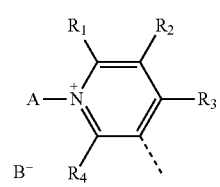

(IIb)

[Chem. 4]

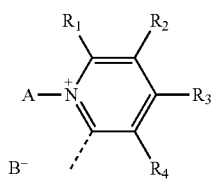

(IIc)

wherein: $Ar_2$ is a monovalent heterocyclic ring which may have a substituent, but $Ar_2$ is not a pyridinium ring; $R_1$ to $R_8$ are each independently a monovalent group which may have a functional group, where the monovalent group may have a substituent; A is a monovalent group which may have a functional group, where the monovalent group may have a substituent; and $B^-$ is a monovalent anion.

Advantageous Effects of Invention

The present invention can provide an electrochromic compound, which has excellent solubility, can be easily highly purified through purification, and is colorless in a discharged state without having an absorption band, when discharged.

BRIEF DESCRIPTION OF DRAWINGS

FIG. 1 is a schematic diagram illustrating one example of a structure of a display element using the electrochromic compound of the present invention.

FIG. 2 is a schematic diagram illustrating another example of a structure of a display element using the electrochromic composition of the present invention.

FIG. 3 is a schematic diagram illustrating one example of a structure of a dimming element using the electrochromic compound of the present invention.

FIG. 4 is a schematic diagram illustrating another example of a structure of a dimming element using the electrochromic composition of the present invention.

FIG. 5 is a diagram depicting absorption spectrums of the display electrode, to which the electrochromic display layer has been formed, produced in Example 27 in the discharged state and the colored state.

FIG. 6 is a diagram depicting absorption spectrums of the display electrode, to which the electrochromic display layer has been formed, produced in Example 28 in the discharged state and the colored state.

FIG. 7 is a diagram depicting absorption spectrums of the display electrode, to which the electrochromic display layer has been formed, produced in Example 29 in the discharged state and the colored state.

FIG. 8 is a diagram depicting absorption spectrums of the display electrode, to which the electrochromic display layer has been formed, produced in Example 30 in the discharged state and the colored state.

FIG. 9 is a diagram depicting absorption spectrums of the display electrode, to which the electrochromic display layer has been formed, produced in Example 31 in the discharged state and the colored state.

FIG. 10 is a diagram depicting absorption spectrums of the display electrode, to which the electrochromic display layer has been formed, produced in Example 32 in the discharged state and the colored state.

FIG. 11A represents the structure of formula (I).

FIG. 11B represents the structure of formula (IIa).
FIG. 11C represents the structure of formula (IIb).
FIG. 11D represents the structure of formula (IIc).

DESCRIPTION OF EMBODIMENTS

The present invention is specifically explained hereinafter. The present invention includes an electrochromic compound having a specific structure, an electrochromic composition, in which the electrochromic compound is supported on an appropriate supporting medium, and a display element and a dimming element using the electrochromic compound or electrochromic composition. The electrochromic compound for use is specifically explained.

(Electrochromic Compound)

The electrochromic compound of the present invention is represented by the following general formula (I):

[Chem. 5]

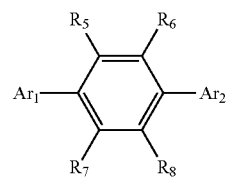

(I)

In the general formula (I), $Ar_1$ is a pyridinium ring having a structure represented by the following general formula (IIa), (IIb), or (IIc):

[Chem. 6]

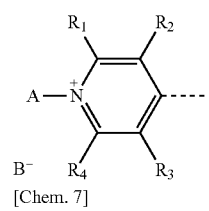

(IIa)

[Chem. 7]

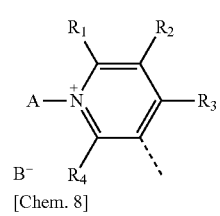

(IIb)

[Chem. 8]

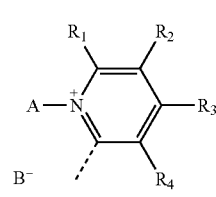

(IIc)

wherein: $Ar_2$ is a monovalent heterocyclic ring which may have a substituent, but $Ar_2$ is not a pyridinium ring, $R_1$ to $R_8$ are each independently a monovalent group which may have a functional group, where the monovalent group may have a substituent; A is a monovalent group which may have a functional group, where the monovalent group may have a substituent; and B⁻ is a monovalent anion.

In the general formulae (I), (IIa), (IIb), and (IIc), the monovalent groups represented by $R_1$ to $R_8$ are each independently a monovalent group selected from a hydrogen atom, a halogen atom (e.g., a fluorine atom, a chlorine atom, a bromine atom, and an iodine atom), a hydroxyl group, a nitro group, a cyano group, a carboxyl group, a carbonyl group, an amide group, an aminocarbonyl group, a sulfonic acid group, a sulfonyl group, a sulfone amide group, an aminosufonyl group, an amino group, an alkyl group, an alkenyl group, an alkynyl group, an aryl group, an alkoxy group, an aryloxy group, an alkylthio group, an arylthio group, and a heterocyclic group. These monovalent group may each have a substituent.

Specifically, examples of the monovalent groups represented by $R_1$ to $R_8$ in the general formulae (I), (IIa), (IIb),and (IIc) include: a hydrogen atom; a halogen atom; a hydroxyl group; a nitro group; a cyano group; a carboxyl group; an alkoxycarbonyl group which may have a substituent; an aryloxy carbonyl group which may have a substituent; an alkyl carbonyl group which may have a substituent; an aryl carbonyl group which may have a substituent; an amide group; a monoalkylaminocarbonyl group which may have a substituent; a dialkylaminocarbonyl group which may have a substituent; a monoarylaminocarbonyl group which may have a substituent; a diarylaminocarbonyl group which may have a substituent; a sulfonic acid group; am alkoxysulfonyl group which may have a substituent; an alkylsulfonyl group which may have a substituent; an arylsulfonyl group which may have a substituent; a sulfone amide group; a monoalkylaminosulfonyl group which may have a substituent; a dialkylaminosulfonyl group which may have a substituent; a monoarylaminosulfonyl group which may have a substituent; a diarylaminosulfonyl group which may have a substituent; an amino group; a monoalkylamino group which may have a substituent; a dialkylamino group which may have a substituent; an alkyl group which may have a substituent; an alkenyl group which may have a substituent; an alkynyl group which may have a substituent; an aryl group which may have a substituent; an alkoxy group which may have a substituent; an aryloxy group which may have a substituent; an alkylthio group which may have a substituent; an arylthio group which may have a substituent; and a heterocyclic group which may have a substituent.

In the general formulae (I), (IIa), (IIb), and (IIc), $Ar_2$ is a monovalent heterocyclic ring which may have a substituent, preferably C2-C50 heterocyclic ring which may have a substituent, more preferably C2-C30 heterocyclic ring which may have a substituent, and particularly preferably C2-C20 heterocyclic ring.

Moreover, examples of constitutional elements thereof include a nitrogen atom, a sulfur atom, an oxygen atom, a silicon atom, and a selenium atom. It is preferred that at least one selected from the group consisting of a nitrogen atom, a sulfur atom, and an oxygen atom be contained.

Specific examples of the monovalent heterocyclic ring $Ar_2$ include monocyclic heterocyclic rings, such as a pyridine ring, a pyrimidine ring, a pyridazine ring, a pyrazine ring, tetrazine, a thiophene ring, a furan ring, pyrrole, imidazole, pyrazole, a thiazole ring, an oxazole ring, isooxazole, an oxadiazole ring, a triazine ring, a tetrazole ring, and a triazole ring. Moreover, examples of polycyclic heterocyclic ring as the monovalent heterocyclic ring $Ar_2$ include quinoline, isoquinoline, quinazoline, phthalazine, indole, benzothiophene, benzofuran, benzoimidazole, benzothiodiazole, acridine, phenoxazine, phenothiazine, carbazole, benzodithiophene, and benzodifuran. These may be substituted with substituents the same as $R_1$ to $R_8$.

In the general formulae (I), (IIa), (IIb), and (IIc), the monovalent groups represented by A are each independently a monovalent group which may have a functional group selected from an alkyl group, an alkenyl group, an alkynyl group, and an aryl group. These monovalent groups may have a substituent.

In the general formulae (I), (IIa), (IIb), and (IIc), B is anion. The anions represented by B⁻ are not particularly limited, as long as the anions each stably form a pair with a cation site. The anions are each preferably a Br ion (Br⁻), a Cl ion (Cl⁻), a I ion (I⁻), a OTf (triflate) ion (OTf⁻), a ClO₄ ion (ClO₄⁻), a PF₆ ion (PF₆⁻), or a BF₄ ion (BF₄⁻). Among them, a halogen atom, or a triflate group is preferable, and a chlorine atom, a bromine atom, an iodine atom, or a triflate group is more preferable.

The monovalent groups represented by $R_1$ to $R_8$ can provide a resulting electrochromic compound with solubility to a solvent, and therefore an element production process using the electrochromic compound becomes easy.

A more preferred embodiment of the electrochromic compound is a structure represented by the following general formula (Ia), where the substituent $Ar_1$ is represented by the general formula (IIa). The structure where a para-position is substituted is preferable in view of stability of a colored state, coloring density, and repeating stability.

[Chem. 9]

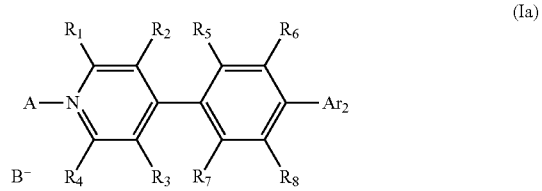

(Ia)

The substituents in the general formula (Ia) are the same as described earlier. As for the particularly preferred embodiment, $Ar_2$ is nitrogen-containing heterocyclic. A reason thereof is not clear, but it is assumed that the presence of the nitrogen atom stabilize the charge, and as a result, a colored state is stabilized. Specific examples thereof include monocyclic nitrogen-containing heterocyclic ring, such as a pyrimidine ring, a pyridazine ring, a pyrazine ring, tetrazine, pyrrole, imidazole, pyrazole, a thiazole ring, an oxazole ring, isooxazole, an oxadiazole ring, a triazine ring, a tetrazole ring, and a triazole ring. Moreover, examples of polycyclic nitrogen-containing heterocyclic ring as the nitrogen-containing heterocyclic ring include quinoline, isoquinoline, quinazoline, phthalazine, indole, benzoimidazole, benzothiodiazole, acridine, phenoxazine, phenothiazine, and carbazole.

The monovalent groups represented by $R_1$ to $R_8$ are each preferably a hydrogen atom;

a halogen atom; a hydroxyl group; a nitro group; a cyano group; a carboxyl group; an amino group; a monoalkylamino group which may have a substituent; a dialkylamino group which may have a substituent; an alkyl group which may have a substituent; an alkenyl group which may have a substituent; an alkynyl group which may have a substituent; an aryl group which may have a substituent; an alkoxy group which may have a substituent; an aryloxy group which may have a substituent; an alkylthio group which may have a substituent; an arylthio group which may have a substituent; or a heterocyclic group which may have a substituent. The monovalent groups represented by $R_1$ to $R_8$ are each more preferably a hydrogen atom; a halogen atom; a cyano group; an alkyl group which may have a substituent; an aryl group which may have a substituent; an alkoxy group which may have a substituent; an aryloxy group which may have a substituent; or a heterocyclic group which may have a substituent The most preferably, the monovalent groups represented by $R_1$ to $R_8$ are each a hydrogen atom; a halogen atom; a cyano group; an alkyl group which may have a substituent; an aryl group which may have a substituent; or a heterocyclic group which may have a substituent.

Moreover, the monovalent groups represented by A are each independently a monovalent group which may have a functional group selected from an alkyl group, an alkenyl group, an alkynyl group, and an aryl group. The monovalent group may have a substituent. The monovalent group preferably has a structure containing either or both an alkyl group, and an aryl group as a partial structure, more preferably has a structure containing only an alkyl group as a partial structure.

In the general formulae (IIa), (IIb), and (IIc), moreover, it is preferred that the monovalent group contain a functional group capable of directly or indirectly binding to a hydroxyl group, the functional group be at least one selected from the group consisting of a phosphonic acid group, a phosphoric acid group, a carboxylic acid group, a silyl group, and a silanol group.

—Synthesis of Electrochromic Compound—

A synthesis method of the electrochromic compound of the present invention, which is represented by the general formula (I), is specifically explained.

The electrochromic compound is obtained, for example, by allowing a benzene compound represented by the following general formula (III), a pyridine compound represented by the following general formulae (IVa), (IVb), or (IVc), a heterocyclic compound represented by the following general formula (V), and a metal catalyst, such as a palladium catalyst, and a nickel catalyst, to react through a cross-coupling reaction in an appropriate solvent with a base. Note that, a base is not necessarily required in all cases.

A target product can be attained by reacting the compound (III) with any one of the compound (IVa), (IVb), or (IVc), or the compound (V) first, followed by reacting with the other remained compound. The order for reacting the compounds is not limited. Moreover, there may be a case where it is better to replace the substituents X and Y for use to attain the better result, in view of stability and reactivity of the compound.

[Chem. 10]

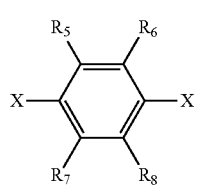

(III)

(In the general formula (III), $R_5$ to $R_8$ are as described earlier; and X is a halogen atom, preferably a chlorine atom, a bromine atom, or an iodine atom, and particularly preferable a bromine atom or an iodine atom.)

[Chem. 11]

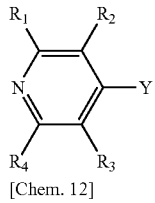

(IVa)

[Chem. 12]

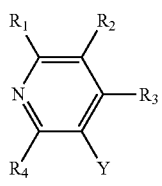

(IVb)

[Chem. 13]

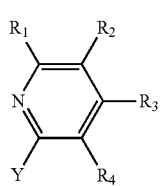

(IVc)

(In the general formulae (IVa), (IVb), and (IVc), $R_1$ to $R_4$ are as described earlier; Y is a boric acid group represented by $B(OH)_2$, a boric acid ester where two hydrogen atoms from two hydroxyl groups of pinacol are taken off, and substituted with a bottom atom, a trimethylstannyl group, or a tributylstannyl group.)

[Chem. 14]

$$Ar_2\text{—}X \qquad (V)$$

(In the general formula (V), $Ar_2$ is a monovalent heterocyclic ring which may have a substituent, but $Ar_2$ is not a pyridinium ring; and X is the same as in the general formula (IV).)

Subsequently, the compound obtained by the reaction is allowed to react with a compound A-B in an appropriate solvent, to thereby synthesize the electrochromic compound of the present invention represented by the following general formula (I).

[Chem. 15]

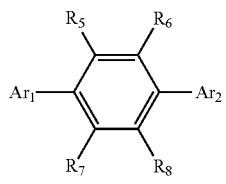

(I)

In the general formula (I), $Ar_1$ is a pyridinium ring having a structure represented by the following general formula (IIa), (IIb), or (IIc):

[Chem. 16]

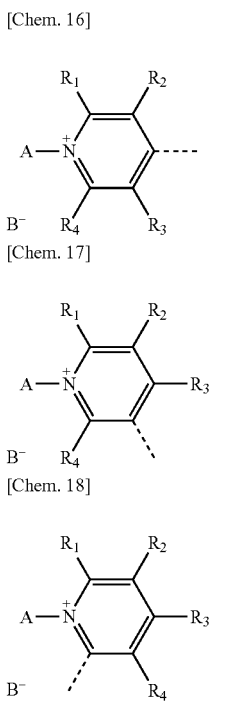

(IIa)

[Chem. 17]

(IIb)

[Chem. 18]

(IIc)

wherein: $Ar_2$ is a monovalent heterocyclic ring which may have a substituent, but $Ar_2$ is not a pyridinium ring, $R_1$ to $R_8$ are each independently a monovalent group which may have a functional group, where the monovalent group may have a substituent; A is a monovalent group which may have a functional group, where the monovalent group may have a substituent; and $B^-$ is a monovalent anion.

The solubility of a resulting compound, or adsorption ability thereof to bearing particles can be controlled by appropriately changing the substituent A. Moreover, the efficiency of a quaternization reaction with a pyridinium ring can be controlled by appropriately changing the anion $B^-$.

A solvent used for the reaction is appropriately selected depending on the intended purpose without any limitation, but the solvent is preferably a polar solvent, and more preferably an aprotic polar solvent. Examples of the solvent include acetone, acetonitrile, dimethyl formamide, dimethyl acetoamide, N-methylpyrrolidone, dioxane, and tetrahydrofuran.

Only the terminal pyridine ring being quaternized is a characteristic of the electrochromic compound of the present invention, and is a preferable embodiment. However, a case where a nitrogen-containing ring, excluding pyridine, is introduced at the heterocyclic site by substitution can be expected.

In the case where a plurality of nitrogen-containing rings are contains, a quaternization reaction can be selectively performed on the predetermined nitrogen-containing ring by setting reaction conditions considering the basicity of the ring, and influence of steric hindrance. The basicity of pyridine is substantially stronger than other nitrogen-containing rings (e.g., pyrimidine, and triazine). In case of quinolone or isoquinoline, moreover, influence of steric hindrance of the adjacent hydrogen (peri-position) is large. As for these insights, the conditions described in New Edition Heterocyclic Compound, Basic, Application, and Development (Technical Science Books of Kodansha Scientific Ltd.) can be referred.

Based on these insights, a selective quaternization reaction to the pyridinium ring sites (IIa), (IIb), (IIc) is successfully performed in a group of the compounds of the present invention.

The purification of the crude product after the reaction can be performed by various purification methods known in the art. Specific examples thereof include solvent washing, recrystallization, column chromatography, reprecipitation, and sublimation purification.

The electrochromic compound of the present invention has excellent solubility compared to conventional compound, and by-products (e.g., raw materials) can be easily separated from the electrochromic compound. Therefore, there tends to be a difference between the solubility of the by-products, and the solubility of the target product. The more preferred purification method is washing with an appropriate solvent. As for the solvent, for example, acetone, 2-propanol, acetonitrile, hexane, or a mixed solvent thereof can be used.

Specific examples of a base skeleton, the monovalent group A, and the anion $B^-$ of the electrochromic compound of the present invention are depicted below. Specifically, specific examples of the actual electrochromic compound include compounds in each of which the monovalent A and the anion $B^-$ are appropriately bonded to the base skeleton, but the electrochromic compound of the present invention is not limited to these examples. Note that, tBu denotes a tertiary butyl group, Me denotes a methyl group, and Et is an ethyl group.

[Chem.19]

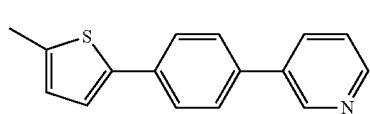

(III-1)

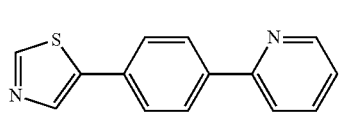

(III-2)

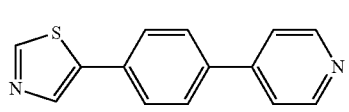

(III-3)

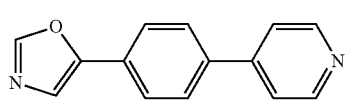

(III-4)

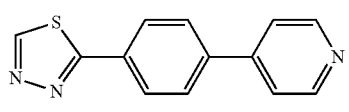

(III-5)

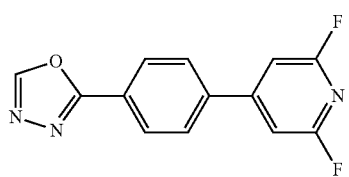

(III-6)

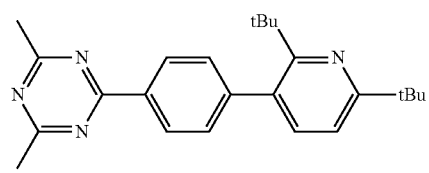
(III-7)
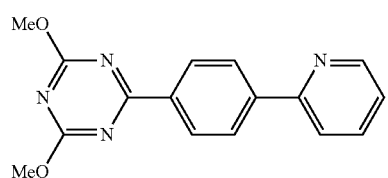
(III-8)
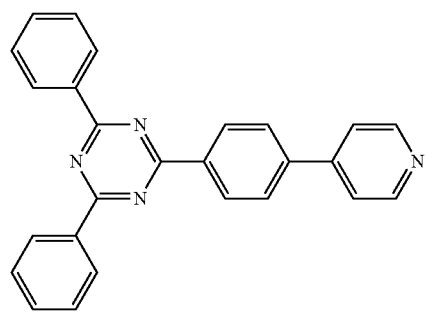
(III-9)
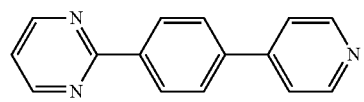
(III-10)
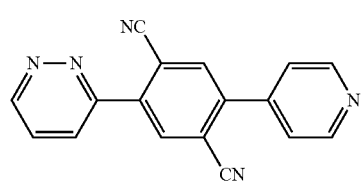
(III-11)
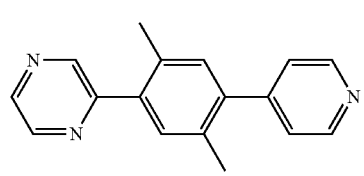
(III-12)
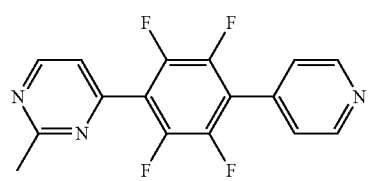
(III-13)
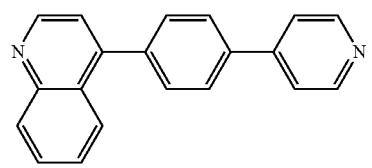
(III-14)
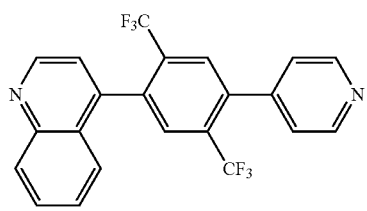
(III-15)
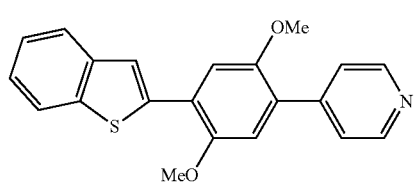
(III-16)
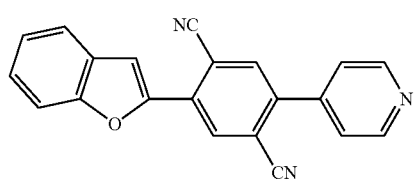
(III-17)
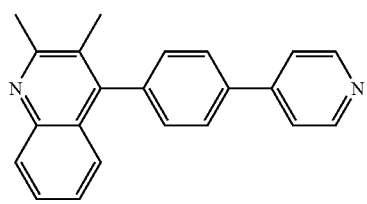
(III-18)
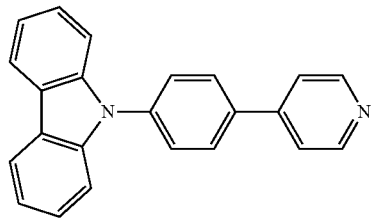
(III-19)
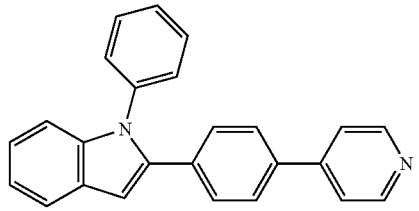
(III-20)
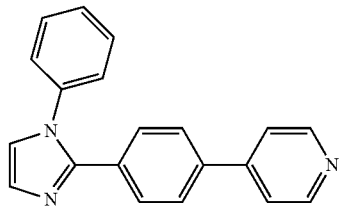
(III-21)

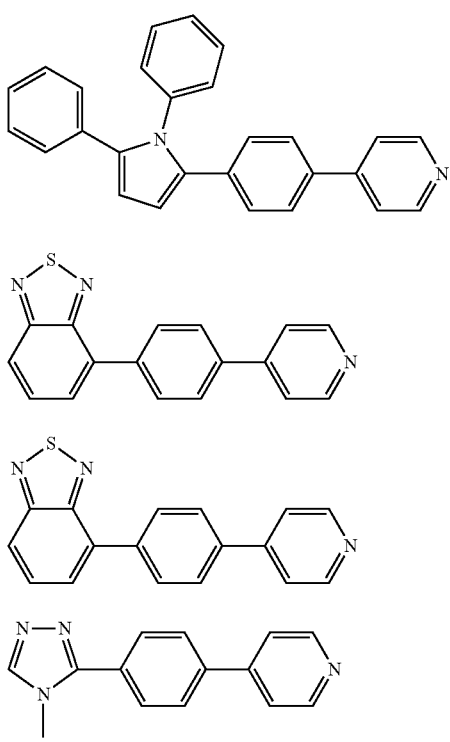

TABLE 1

| | | |
|---|---|---|
| I⁻ *⁻⁻ | Formula (IV-1) | |
| I⁻ *⁻⁻⁻CF₃ | Formula (IV-2) | |
| Cl⁻ *⁻⁻⁻⁻⁻⁻⁻PO(OH)₂ | Formula (IV-3) | |
| Br⁻ *⁻⁻⁻⁻⁻⁻⁻⁻PO(OH)₂ | Formula (IV-4) | |
| OTf⁻ *⁻⁻PO(OH)₂ | Formula (IV-5) | |
| OTf⁻ *⁻⁻CF₃ | Formula (IV-6) | |
| Br⁻ *-C₆H₄-CH₂-PO(OH)₂ | Formula (IV-7) | |
| Cl⁻ *⁻COOH | Formula (IV-8) | |
| Cl⁻ *⁻⁻⁻⁻⁻COOH | Formula (IV-9) | |
| Br⁻ *⁻⁻⁻⁻⁻⁻SiOEt₃ | Formula (IV-10) |
| Br⁻ *⁻⁻⁻⁻⁻⁻SiOMe₃ | Formula (IV-11) |
| BF₄⁻ *⁻⁻⁻⁻⁻⁻SiOEt₃ | Formula (IV-12) |
| PF₆⁻ *-C₆H₄-CH₂-PO(OH)₂ | Formula (IV-13) |

In the table above. * denotes a bonding site of the pyridinium ring with a nitrogen atom.

The anion B⁻ can be replaced with a desired anion by performing an appropriate process.

(Electrochromic Composition)

The electrochromic composition of the present invention contains the electrochromic compound of the present invention, and an electrically conductive or semiconductive nanostructure, where the electrochromic compound is bonded to, or adsorbed on the electrically conductive or semiconductive nanostructure.

When the electrochromic composition of the present invention is used in an electrochromic display element, the resulting electrochromic display element colors in black, and has a memory effect of an image displayed, specifically, such the electrochromic display element is excellent in color image retention properties.

The electrically conductive or semiconductive nanostructure is a structure having nano-scale irregularities, such as nano particles, and a nano porous structure.

In the case where the monovalent group A contains a functional group capable of directly or indirectly binding to a hydroxyl group as mentioned earlier, the electrochromic compound easily forms a complex with the nanostructure, as the electrochromic compound contains a sulfonic acid group, a phosphoric acid group, or a carboxyl group as a bond or an adsorption structure. Therefore, a resulting electrochromic composition has excellent color image retention properties. A plurality of the sulfonic acid group, phosphoric acid group, or carboxyl group may be contained in the electrochromic compound. When the electrochromic compound of the present invention contains a silyl group or a silanol group, the electrochromic compound is bonded to the nanostructure through a siloxane bond, hence the bond is rigid. Therefore, a stable electrochromic composition is attained. The siloxane bond mentioned above is a chemical bond through a silicon atom and an oxygen atom. Moreover, a bonding method or embodiment of the electrochromic composition is not particularly limited, as long as the electrochromic composition has a structure where the electrochromic compound and the nanostructure are bonded through the siloxane bond.

As for a material constituting the electrically conductive or semiconductive nanostructure, metal oxide is preferable in view of transparency or conductivity thereof.

Examples of the metal oxide include titanium oxide, zinc oxide, tin oxide, zirconium oxide, cerium oxide, yttrium oxide, boron oxide, magnesium oxide, strontium titanate, potassium titanate, barium titanate, calcium titanate, calcium oxide, ferrite, hafnium oxide, indium oxide, tungsten oxide, iron oxide, copper oxide, nickel oxide, cobalt oxide, barium oxide, strontium oxide, vanadium oxide, aluminosilicic acid, calcium phosphate, and aluminosilicate. These may be used alone, or in combination.

Among them, preferred is the one selected from titanium oxide, zinc oxide, tin oxide, zirconium oxide, iron oxide, magnesium oxide, indium oxide, and tungsten oxide, or a mixture thereof, in view of electric properties, such as electric conductivity, or physical properties, such as optical characteristics. Especially when titanium oxide is used as the metal oxide, more excellent coloring-discharging response speed can be attained.

The metal oxide is preferably metal oxide particles having the average primary particle diameter of 30 nm or smaller. As the average primary particle diameter of the metal oxide particles is smaller, the transmittance of light to the metal oxide improves more, and a shape of the nanostructure having a large surface area per unit volume (referred to as "specific surface area" hereinafter) is used. As the metal oxide has a large specific surface area, the electrochromic compound is more efficiently born on the nanostructure, and therefore it is possible to realize a multi-color display having an excellent contrast ratio of coloring and discharging. The specific surface area of the nanostructure is appropriately selected depending on the intended purpose without any limitation, but the specific surface area thereof is preferably 100 $m^2/g$ or greater.

(Display Element)

The display element of the present invention contains a display electrode, a counter electrode provided to face the display element with a space between the display electrode and the counter electrode, and an electrolyte provided between the display element and the counter electrode, where a display layer containing the electrochromic compound of the present invention or the electrochromic composition of the present invention is provided at a surface of the display electrode.

The display element of the present invention uses the electrochromic compound of the present invention, or the electrochromic composition of the present invention, and thus a monochromic display element having high white reflectance and a high contrast can be provided.

The display element of the present invention contains a display layer containing the electrochromic compound of the present invention, i.e., the compound represented by the general formula (I), or the electrochromic compound represented by the general formula (Ia).

FIG. 1 illustrates an example of a structure of a display element using the electrochromic compound of the present invention. The display element 10 illustrated in FIG. 1 contains a display electrode 1, a counter electrode 2 provided to face the display electrode 1 with a space between the display electrode 1 and the counter electrode 2, and an electrolyte 3, which is provided between both electrodes (the display electrode 1 and the counter electrode 2), and in which the electrochromic compound (organic electrochromic compound) 4 of the present invention is dissolved. In the display element, the electrochromic compound colors and discharges through an oxidation-reduction reaction only at a surface of the electrode.

FIG. 2 illustrates another example of a structure of a display element using the electrochromic compound of the present invention.

The display element 20 of the present invention contains a display electrode 1, a counter electrode 2 provided to face the display electrode 1 with a space between the display electrode 1 and the counter electrode 2, and an electrolyte 3 provided between both electrodes (the display electrode 1 and the counter electrode 2), in which a display layer 5 containing the electrochromic composition 4a of the present invention is provided at a surface of the display electrode 1. Moreover, a white reflection layer 6 composed of white particles is provided at the side of the display electrode 1 of the counter electrode 2.

As for an electrochromic compound in the electrochromic composition of the present invention, an electrochromic compound containing a functional group (adsorption group) capable of directly or indirectly binding to a hydroxyl group, i.e., a linking group, can be used. Therefore, the linking group is bonded to an electrically conductive or semiconductive nanostructure, to thereby constitute the electrochromic composition. The electrochromic composition is provided on the display electrode 1 in the form of a layer, to thereby form the display layer 5.

Constitutional materials used for the electrochromic display elements 10, 20 according to the embodiments of the present invention are explained hereinafter. As for a material constituting the display electrode 1, a transparent, electrically conductive substrate is preferably used. As for the transparent, electrically conductive substrate, a substrate prepared by coating glass, or a plastic film with a transparent, electrically conductive film is preferable.

The transparent, electrically conductive film material is not particularly limited as long as it is a material having conductivity, but a transparent conductivity having excellent transparency and conductivity is used, as it is necessary to secure transparency to light. Use of the aforementioned material can enhance visibility of color to be colored.

As for the transparent, electrically conductive material, an inorganic material, such as tin-doped indium oxide (abbr.: ITO), fluorine-doped tin oxide (abbr.: FTO), and antimony-doped tin oxide (abbr.: ATO), can be used. An inorganic material containing indium oxide (referred to as In oxide, hereinafter), tin oxide (referred to as Sn oxide, hereinafter), or zinc oxide (referred to as Zn oxide, hereinafter) is particularly preferable as the transparent, electrically conductive material. In oxide, Sn oxide, and Zn oxide are materials, with which a film can be easily formed by sputtering, and which give excellent transparency and electric conductivity. Among them, InSnO, GaZnO, SnO, $In_2O_3$, and ZnO are preferable.

Examples of a material constituting a display substrate (not depicted with a numeral reference) to which the display electrode 1 is provided include glass, and a plastic. Use of a plastic film as the display substrate can produce a light and flexible display element.

As for the counter electrode 2, a transparent, electrically conductive film, such as ITO, FTO, and zinc oxide, or an electrically conductive metal film, such as zinc, and platinum, or carbon is used. The counter electrode 2 is also typically formed on a counter substrate (not depicted with a numeral reference). The counter substrate is also preferably glass, or a plastic film. In the case where a metal plate, such as titanium, and zinc, is used as the counter electrode 2, the counter electrode 2 also functions as a substrate.

In the case where a material constituting the counter electrode 2 is a material that causes a reverse reaction of the oxidation-reduction reaction caused by the electrochromic composition of the display layer, stable coloring and discharging are realized. Specifically, reactions of coloring and discharging in the display layer 5 containing the electrochromic composition are more stable, when a material that causes a reduction reaction is used as the counter electrode 2 in the case where the electrochromic composition is colored by oxidation, and a material that causes an oxidation reaction is used as the counter electrode 2 in the case where the electrochromic composition is colored by reduction.

As for a material constituting the electrolyte 3, a material, in which a supporting electrolyte is dissolved in a solvent, is typically used.

As for the supporting electrolyte, for example, an inorganic ionic salt (e.g., alkali metal salt, and alkaline earth metal salt), a quaternary ammonium salt, an acid supporting electrolyte, or a base supporting electrolyte can be used. Specific examples of the supporting electrolyte include $LiClO_4$, $LiBF_4$, $LiAsF_6$, $LiPF_6$, $CF_3SO_3Li$, $CF_3$ COOLi, KCl, $NaClO_3$, NaCl, $NaBF_4$, NaSCN, $KBF_4$, $Mg(ClO_4)_2$, and $Mg(BF_4)_2$.

Examples of the solvent include propylene carbonate, acetonitrile, gamma-butyrolactone, ethylene carbonate, sulfolane, dioxolane, tetrahydrofuran, 2-methyltetrahydrofuran, dimethyl sulfoxide, 1,2-dimethoxyethane, 1,2-ethoxymethoxyethane, polyethylene glycol, and alcohols.

The electrolyte is not limited to a liquid electrolyte, in which a supporting electrolyte is dissolved in a solvent. An electrolyte in the form of a gel, or a solid electrolyte, such as a polymer electrolyte, can be used as the electrolyte. As for a solid electrolyte, for example, there is a perfluorosulfonic acid polymer film. The solution-based electrolyte has an advantage that it has high ion conductivity. The solid electrolyte is suitable for producing an electrode having high durability without causing deterioration.

In the case where the display element of the present invention is used as a reflective display element, as in FIG. 2, the white reflection layer 6 is preferably provided between the display electrode 1 and the counter electrode 2. The simplest method for producing the white reflection layer 6 is a method containing dispersing white pigment particles in a resin, and applying the resultant onto the counter electrode 2 by coating.

As for the white pigment particles, particles formed of typical metal oxide are used. Specific examples thereof include titanium oxide, aluminium oxide, zinc oxide, silicon oxide, cesium oxide, and yttrium oxide. Moreover, the electrolyte can also function as the white reflection layer when white pigment particles are mixed in the polymer electrolyte.

A driving method of the display elements 10, 20 is not particularly limited, and any method can be used, as long as the predetermined voltage and current can be applied. Use of a passive driving method can produce a low-cost display element. Moreover, use of an active driving method can realize a display of high precision, and high speed. The active driving can be easily achieved by providing an active driving element on the counter substrate.

(Dimming Element)

The dimming element of the present invention contains a display electrode, a counter electrode provided to face the display electrode with a space between the display electrode and the counter electrode, and an electrolyte provided between the display electrode and the counter electrode, where the electrochromic compound of the present invention or the electrochromic composition of the present invention is provided at a surface of the display electrode.

In the dimming element of the present invention, the display electrode, the counter electrode, and the electrolyte are transparent.

The dimming element of the present invention uses the electrochromic compound of the present invention or the electrochromic composition of the present invention, and thus a monochromic dimming element having high transparency and a high contrast can be provided.

FIG. 3 illustrates an example of a structure of a dimming element using the electrochromic compound of the present invention. The dimming element 30 illustrated in FIG. 3 contains a display electrode 1, a counter electrode 2 provided to face the display electrode 1 with a space between the display electrode 1 and the counter electrode 2, and an electrolyte 3, which is provided between both electrodes (the display electrode 1 and the counter electrode 2), and in which the electrochromic compound (organic electrochromic compound) 4 of the present invention is dissolved. In the dimming element, the electrochromic compound colors and discharges through an oxidation-reduction reaction only at a surface of the electrode. A transparency of the dimming element as a whole is particularly important.

FIG. 4 illustrates another example of a structure of a dimming element using the electrochromic composition of the present invention.

The dimming element 40 of the present invention contains a display electrode 1, a counter electrode 2 provided to face the display electrode 1 with a space between the display electrode 1 and the counter electrode 2, and an electrolyte 3 provided between both electrodes (the display electrode 1 and the counter electrode 2), in which a display layer 5 containing the electrochromic composition 4a of the present invention is provided at a surface of the display electrode 1.

As for an electrochromic compound in the electrochromic composition of the present invention, an electrochromic compound containing a functional group (adsorption group) capable of directly or indirectly binding to a hydroxyl group, i.e., a linking group, can be used. Therefore, the linking group is bonded to an electrically conductive or semiconductive nanostructure, to thereby constitute the electrochromic composition. The electrochromic composition is provided on the display electrode 1 in the form of a layer, to thereby form the display layer 5.

Constitutional materials used for the electrochromic dimming elements 30, 40 according to the embodiments of the present invention are explained hereinafter.

As for a material constituting the display electrode 1, a transparent, electrically conductive substrate is used. As for the transparent, electrically conductive substrate, a substrate prepared by coating glass, or a plastic film with a transparent, electrically conductive film is preferable.

The transparent, electrically conductive film material is not particularly limited as long as it is a material having conductivity, but a transparent conductivity having excellent transparency and conductivity is used, as it is necessary to secure transparency to light. Use of the aforementioned material can enhance visibility of color to be colored.

As for the transparent, electrically conductive material, an inorganic material, such as tin-doped indium oxide (abbr.: ITO), fluorine-doped tin oxide (abbr.: FTO), and antimony-doped tin oxide (abbr.: ATO), can be used. An inorganic material containing indium oxide (referred to as In oxide, hereinafter), tin oxide (referred to as Sn oxide, hereinafter), or zinc oxide (referred to as Zn oxide, hereinafter) is particularly preferable as the transparent, electrically conductive material. In oxide, Sn oxide, and Zn oxide are materials, with which a film can be easily formed by sputtering, and which give excellent transparency and electric conductivity. Moreover, the particularly preferred materials are InSnO, GaZnO, SnO, $In_2O_3$, and ZnO.

Examples of a material constituting a display substrate (not depicted with a numeral reference) to which the display electrode 1 is provided include glass, and a plastic. Use of a plastic film as the display substrate can produce a light and flexible display element.

Similarly to the display electrode 1, a transparent, electrically conductive substrate is also used for the counter electrode 2. As for the transparent, electrically conductive substrate, a substrate, in which glass or a plastic film coated with a transparent, electrically conductive film, is preferable.

The transparent, electrically conductive film material is not particularly limited as long as it is a material having conductivity, but a transparent conductivity having excellent transparency and conductivity is used, as it is necessary to secure transparency to light. Use of the aforementioned material can enhance visibility of color to be colored.

As for the transparent, electrically conductive material, an inorganic material, such as tin-doped indium oxide (abbr.: ITO), fluorine-doped tin oxide (abbr.: FTO), and antimony-doped tin oxide (abbr.: ATO), can be used. An inorganic material containing indium oxide (referred to as In oxide, hereinafter), tin oxide (referred to as Sn oxide, hereinafter), or zinc oxide (referred to as Zn oxide, hereinafter) is particularly preferable as the transparent, electrically conductive material. In oxide, Sn oxide, and Zn oxide are materials, with which a film can be easily formed by sputtering, and which give excellent transparency and electric conductivity. Moreover, the particularly preferred materials are InSnO, GaZnO, SnO, $In_2O_3$, and ZnO.

Similarly to the display electrode 1, examples of a material constituting a counter substrate (not depicted with a numeral reference) to which the counter electrode 2 is provided include glass, and a plastic. Use of a plastic film as the counter substrate can produce a light and flexible display element.

In the case where a material constituting the counter electrode 2 is a material that causes a reverse reaction of the oxidation-reduction reaction caused by the electrochromic composition of the display layer, stable coloring and discharging are realized. Specifically, reactions of coloring and discharging in the display layer 5 containing the electrochromic composition are more stable, when a material that causes a reduction reaction is used as the counter electrode 2 in the case where the electrochromic composition is colored by oxidation, and a material that causes an oxidation reaction is used as the counter electrode 2 in the case where the electrochromic composition is colored by reduction.

As for a material constituting the electrolyte 3, a material, in which a supporting electrolyte is dissolved in a solvent, is typically used. In case of the dimming element, particularly, the electrolyte 3 is colorless, and transparent.

As for the supporting electrolyte, for example, an inorganic ionic salt (e.g., alkali metal salt, and alkaline earth metal salt), a quaternary ammonium salt, an acid supporting electrolyte, or a base supporting electrolyte can be used. Specific examples of the supporting electrolyte include $LiClO_4$, $LiBF_4$, $LiAsF_6$, $LiPF_6$, $CF_3SO_3Li$, $CF_3COOLi$, KCl, $NaClO_3$, NaCl, $NaBF_4$, NaSCN, $KBF_4$, $Mg(ClO_4)_2$, and $Mg(BF_4)_2$.

Examples of the solvent include propylene carbonate, acetonitrile, gamma-butyrolactone, ethylene carbonate, sulfolane, dioxolane, tetrahydrofuran, 2-methyltetrahydrofuran, dimethyl sulfoxide, 1,2-dimethoxyethane, 1,2-ethoxymethoxyethane, polyethylene glycol, and alcohols.

The electrolyte is not limited to a liquid electrolyte, in which a supporting electrolyte is dissolved in a solvent. An electrolyte in the form of a gel, or a solid electrolyte, such as a polymer electrolyte, can be used as the electrolyte. As for a solid electrolyte, for example, there is a perfluorosulfonic acid polymer film. The solution-based electrolyte has an advantage that it has high ion conductivity. The solid electrolyte is suitable for producing an electrode having high durability without causing deterioration.

A driving method of the dimming elements 30, 40 is not particularly limited, and any method can be used, as long as the predetermined voltage and current can be applied. Use of a passive driving method can produce a low-cost dimming element. Moreover, use of a transparent active driving element can perform dimming with high precision at high speed. Examples of the transparent active driving element include IGZO.

EXAMPLES

The electrochromic compound and electrochromic composition of the present invention, and a display element or dimming element using the electrochromic compound or electrochromic composition are explained through examples hereinafter, but the present invention is not limited to these examples.

Example 1

Synthesis of Compound 1b)

(a) Synthesis of Compound 1a

[Chem. 20]

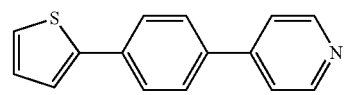

Compound 1a

A flask was charged with 2-bromothiophene (815 mg, 5 mmol), and 4-(4-pyridyl)phenylboronic acid (manufactured by Wako Pure Chemical Industries, Ltd., 1.19 g, 6 mmol), and the flask was purged with argon gas. Thereafter, dioxane (60 mL) degassed with argon gas, and bis(triphenylphosphine)palladium(II) dichloride (0.25 mmol, 175 mg) were added to the flask. After bubbling the obtained solution with argon gas, a 2M potassium carbonate aqueous solution (12 mL) was added to the solution, and the resultant was heated at 100° C. for 8 hours with stirring. The content of the flask was filtered using celite. The resulting filtrate was concentrated to obtain a crude product. Specifically, to the resulting filtrate, water and chloroform were added to separate an organic layer. Thereafter, the resulting water layer was extracted 5 times with chloroform. After washing the combined organic layer with a saturated saline solution, the layer was dried with sodium sulfate, to thereby obtain a crude product. The crude product was purified by silica gel chromatography (eluent: chloroform/methanol=95/5), and the obtained solids were recrystallized with chloroform/hexane, to thereby perform purification. The solids collected by filtration were vacuum dried, to thereby yield Compound 1a (yielded amount: 1.01 g, yield: 85%), as pale yellow solids.

$^1$HNMR(500 MHz,$CDCl_3$,δ): 8.67 (d, $J_1$=5.7 Hz, $J_2$=1.7 Hz, 2H), 7.73 (J=6.9 Hz, 2H), 7.68 (J=6.3 Hz, 2H), 7.54 (dd, $J_1$=6.3 Hz, $J_2$=1.8 Hz), 7.40 (dd, $J_1$=6.3 Hz, $J_2$=1.2 Hz, 1H), 7.34 (dd, $J_1$=6.3 Hz, $J_2$=1.1 Hz, 1H), 7.12(t, J=4.3 Hz, 1H)

(b) Synthesis of Compound 1b

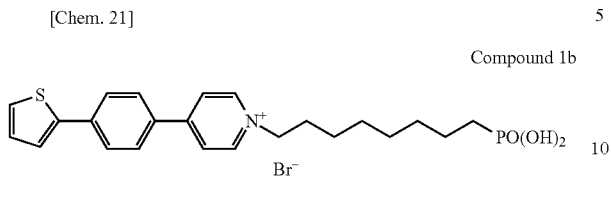
Compound 1b

A flask was charged with Compound 1a (474 mg, 2 mmol), bromooctylphosphonic acid (654 mg, 2.4 mmol), and DMF (15 mL), and the resulting mixture was heated at 100° C. for 5 hours with stirring. The DMF was removed by the reduced pressure. To the residue, 2-propanol was added to precipitate solids. The precipitated solids were collected by filtration, and the collected solids were vacuum dried, to thereby yield Compound 1b as yellow solids (yielded amount: 937 mg, yield: 92%, purity by HPLC: 99.5% (based on peak area)).

Example 2

Synthesis of Compound 2b (a) Synthesis of Compound 2a

[Chem. 22]

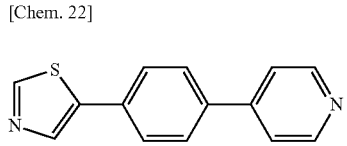
Compound 2a

Compound 2a was obtained (yielded amount: 822 mg, yield: 69%) by carrying out a reaction and purification in the same manner as in Example 1, provided that 2-bromothiophene was replaced with 5-bromothiazole.

$^1$HNMR(500 MHz,CDCl$_3$, δ): 8.81 (s, 1H), 8.70 (dd, J$_1$=4.6 Hz, J$_2$=1.7 Hz, 2H), 8.16 (s, 1H), 7.71 (s, 4H), 7.53 (dd, J$_1$=4.6 Hz, J$_2$=1.7 Hz, 2H)

(b) Synthesis of Compound 2b

[Chem. 23]

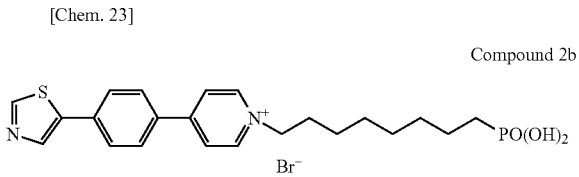
Compound 2b

Compound 2b was obtained (yielded amount: 941 mg, yield: 92%, purity by HPLC: 99.6% (based on peak area)) by carrying out a reaction and purification in the same manner as in Example 1, provided that Compound 1a was replaced with Compound 2a.

Example 3

Synthesis of Compound 3b (a) Synthesis of Compound 3a

[Chem. 24]

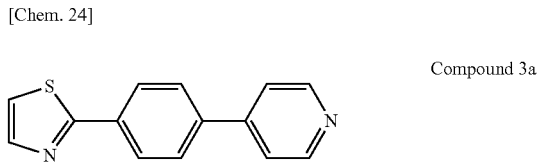
Compound 3a

Compound 3a was obtained (yielded amount: 298 mg, yield: 25%) by carrying out a reaction and purification in the same manner as in Example 1, provided that 2-bromothiophene was replaced with 2-bromothiazole.

$^1$HNMR(500 MHz,CDCl$_3$, δ): 8.70 (dd, J$_1$=4.6 Hz, J$_2$=1.7 Hz, 2H), 8.10 (dd, J$_1$=6.8 Hz, J$_2$=1.7 Hz, 2H), 7.92 (d, J$_1$=2.9 Hz, 1H), 7.74 (dd, J$_1$=6.8 Hz, J$_2$=1.7 Hz, 2H), 7.56(dd, J$_1$=4.6 Hz, J$_2$=1.7 Hz, 2H), 7.39 (d, J$_1$=3.9 Hz, 1H)

(b) Synthesis of Compound 3b

[Chem. 25]

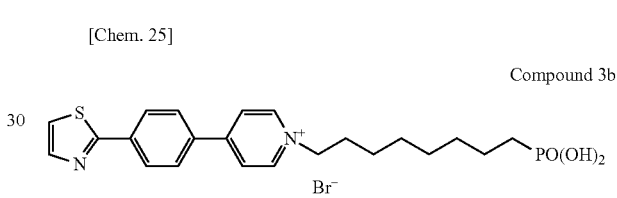
Compound 3b

Compound 3b was obtained (yielded amount: 900 mg, yield: 88%, purity by HPCL: 99.5% (based on peak area)) by carrying out a reaction and purification in the same manner as in Example 1, provided that Compound 1a was replaced with Compound 3a.

Example 4

Synthesis of Compound 4b (a) Synthesis of Compound 4a

[Chem. 26]

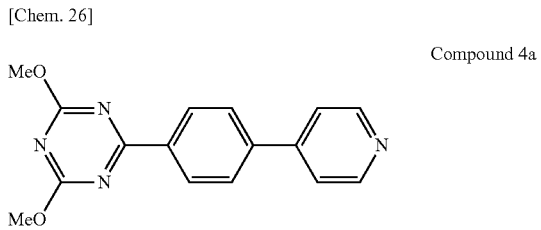
Compound 4a

Compound 4a was obtained (yielded amount: 706 mg, yield: 48%) by carrying out a reaction and purification in the same manner as in Example 1, provided that 2-bromothiophene was replaced with 2-bromo-4,6-dimethoxytriazine.

$^1$HNMR(500 MHz,CDCl$_3$, δ): 8.71 (dd, J$_1$=4.6 Hz, J$_2$=1.7 Hz, 2H), 8.62 (dd, J$_1$=6.9 Hz, J$_2$=1.7 Hz, 2H), 7.77 (dd, J$_1$=6.9 Hz, J$_2$=2.3 Hz, 2H),(dd, J$_1$=4.6 Hz, J$_2$=1.7 Hz, 2H), 4.16 (s, 6H)

(b) Synthesis of Compound 4b

[Chem. 27]

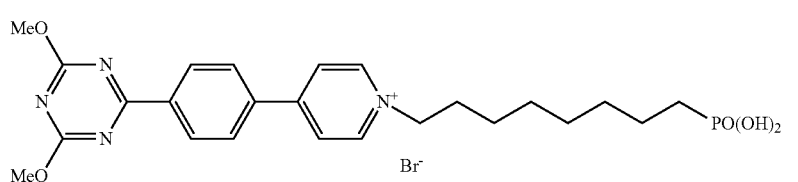

Compound 4b

Compound 4b was obtained (yielded amount: 1.05 g, yield: 93%, purity by HPCL: 99.5% (based on peak area)) by carrying out a reaction and purification in the same manner as in Example 1, provided that Compound 1a was replaced with Compound 4a.

Example 5

Synthesis of Compound 5b (a) Synthesis of Compound 5a

[Chem. 28]

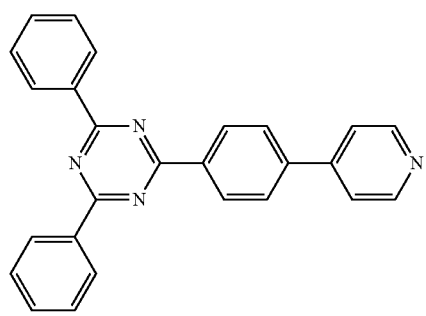

Compound 5a

Compound 5a was obtained (yielded amount: 579 mg, yield: 43%, purity by HPCL: 99.5% (based on peak area)) by carrying out a reaction and purification in the same manner as in Example 1, provided that 2-bromothiophene was replaced with 2-bromo-4,6-diphenyltriazine.

$^1$HNMR(500 MHz, CDCl$_3$, δ): 8.90 (dd, J$_1$=6.3 Hz, J$_2$=1.7 Hz, 2H), 8.80 (dd, J$_1$=8.0 Hz, J$_2$=1.7 Hz, 4H), 8.74 (dd, J$_1$=4.6 Hz, J$_2$=1.7 Hz, 2H), 7.85 (dd, J$_1$=6.3 Hz, J$_2$=1.7 Hz, 2H), 7.58-7.66 (m, 8 H)

(b) Synthesis of Compound 5b

[Chem. 29]

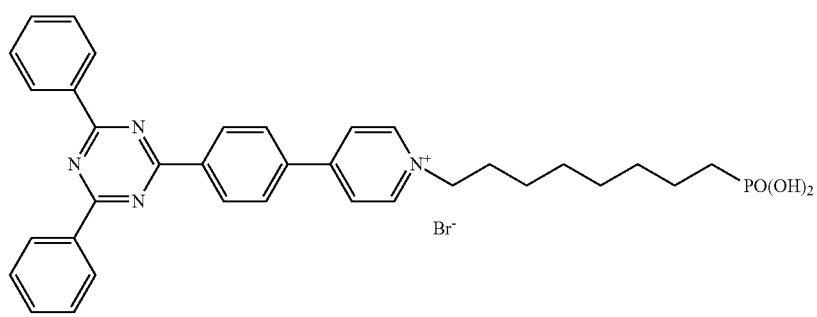

Compound 5b

Compound 5b was obtained (yielded amount: 952 mg, yield: 84%, purity by HPCL: 99.5% (based on peak area)) by carrying out a reaction and purification in the same manner as in Example 1, provided that Compound 1a was replaced with Compound 5a.

Example 6

Synthesis of Compound 6b (a) Synthesis of Compound 6a

[Chem. 30]

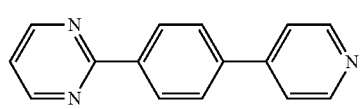

Compound 6a

Compound 6a was obtained (yielded amount: 617 mg, yield: 53%) by carrying out a reaction and purification in the same manner as in Example 1, provided that 2-bromothiophene was replaced with 2-chloropyrimidine.

(b) Synthesis of Compound 6b

[Chem. 31]

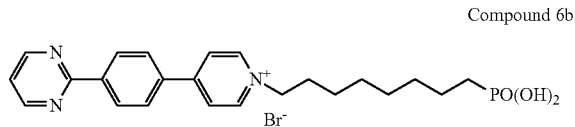

Compound 6b

Compound 6b was obtained (yielded amount: 952 mg, yield: 84%, purity by HPCL: 99.6% (based on peak area)) by carrying out a reaction and purification in the same manner as in Example 1, provided that Compound 1a was replaced with Compound 6a.

Example 7

Synthesis of Compound 7b (a) Synthesis of Compound 7a

[Chem. 32]

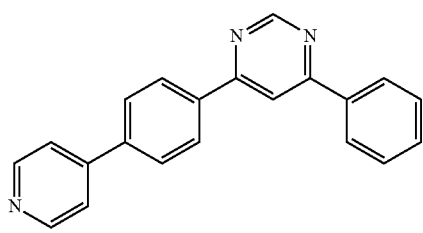

Compound 7a

A flask was charged with 4,6-dichloropyrimidine (740 mg, 5 mmol), and 4-(4-pyridyl)phenylboronic acid (manufactured by Wako Pure Chemical Industries, Ltd., 1.0 g, 5 mmol), and the flask was purged with argon gas. Thereafter, dioxane (60 mL) degassed with argon gas, and bis(triphenylphosphine)palladium(II) dichloride (0.25 mmol, 175 mg) were added to the flask. After bubbling the obtained solution with argon gas, a 2M potassium carbonate aqueous solution (24 mL) was added to the solution, and the resultant was heated at 60° C. for 4 hours with stirring. Subsequently, phenylboronic acid (6 mmol, 731 mg) was added to the solution, and the resultant was heated at 80° C. for 4 hours with stirring. The content of the flask was filtered using celite. The resulting filtrate was concentrated to obtain a crude product. Specifically, to the resulting filtrate, water and chloroform were added to separate an organic layer. Thereafter, the resulting water layer was extracted 5 times with chloroform. After washing the combined organic layer with a saturated saline solution, the layer was dried with sodium sulfate, to thereby obtain a crude product. The crude product was purified by silica gel chromatography (eluent: chloroform/methanol=95/5), and the obtained solids were recrystallized with chloroform/hexane, to thereby perform purification. The solids collected by filtration were vacuum dried, to thereby yield Compound 7a (yielded amount: 1.16 g, yield: 75%) as pale yellow solids.

(b) Synthesis of Compound 7b

[Chem. 33]

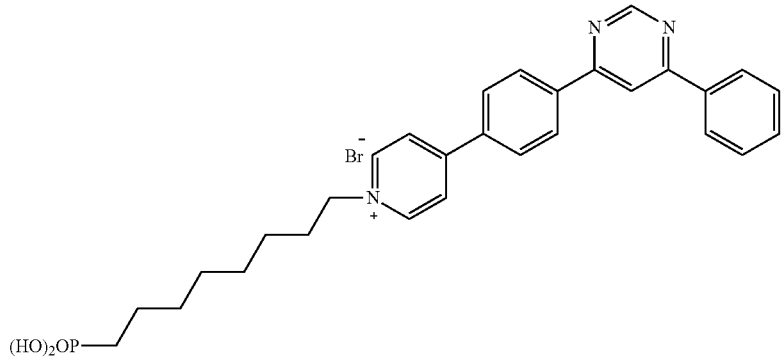

Compound 7b

Compound 7b was obtained (yielded amount: 566 mg, yield: 50%, purity by HPCL: 99.4% (based on peak area)) by carrying out a reaction and purification in the same manner as in Example 1, provided that Compound 1a was replaced with Compound 7a.

Example 8

Synthesis of Compound 8b (a) Synthesis of Compound 8a

[Chem. 34]

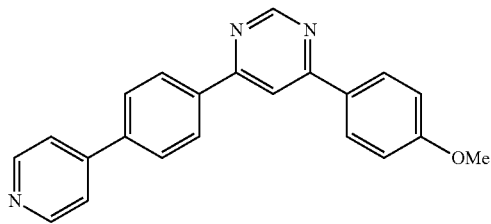

Compound 8a

A flask was charged with 4,6-dichloropyrimidine (740 mg, 5 mmol), and 4-(4-pyridyl)phenylboronic acid (manufactured by Wako Pure Chemical Industries, Ltd., 1.0 g, 5 mmol), and the flask was purged with argon gas. Thereafter, dioxane (60 mL) degas sed with argon gas, and bis(triphenylphosphine)palladium(II) dichloride (0.25 mmol, 175 mg) were added to the flask. After bubbling the obtained solution with argon gas, a 2M potassium carbonate aqueous solution (24 mL) was added to the solution, and the resultant was heated at 60° C. for 4 hours with stirring. Subsequently, 4-methoxyphenylboronic acid (6 mmol, 911 mg) was added to the solution, and the resultant was heated at 80° C. for 4 hours with stirring. The content of the flask was filtered using celite. The resulting filtrate was concentrated to obtain a crude product. Specifically, to the resulting filtrate, water and chloroform were added to separate an organic layer. Thereafter, the resulting water layer was extracted 5 times with chloroform. After washing the combined organic layer with a saturated saline solution, the layer was dried with sodium sulfate, to thereby obtain a crude product. The crude product was purified by silica gel chromatography (eluent: chloroform/methanol=95/5), and the obtained solids were recrystallized with chloroform/hexane, to thereby perform purification. The solids collected by filtration were vacuum dried, to thereby yield Compound 8a (yielded amount: 1.20 g, yield: 71%), as pale yellow solids.

(b) Synthesis of Compound 8b

[Chem. 35]

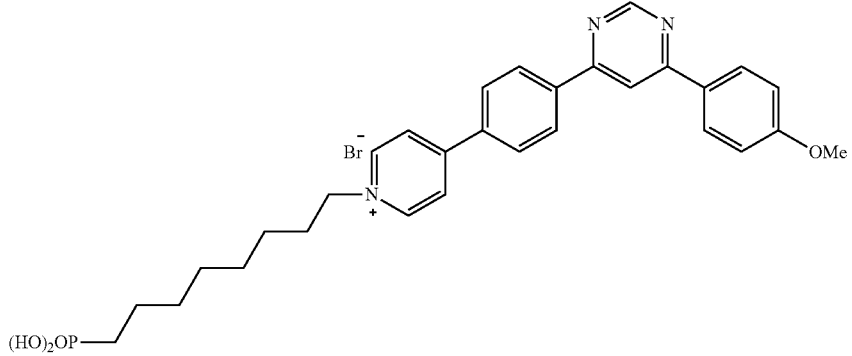

Compound 8b

Compound 8b was obtained (yielded amount: 632 mg, yield: 53%, purity by HPCL: 99.5% (based on peak area)) by carrying out a reaction and purification in the same manner as in Example 1, provided that Compound 1a was replaced with Compound 8a.

Example 9

Synthesis of Compound 9b (a) Synthesis of Compound 9a

[Chem. 36]

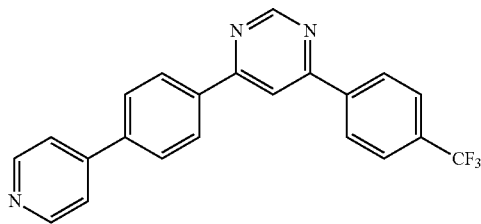

Compound 9a

A flask was charged with 4,6-dichloropyrimidine (740 mg, 5 mmol), and 4-(4-pyridyl)phenylboronic acid (manufactured by Wako Pure Chemical Industries, Ltd., 1.0 g, 5 mmol), and the flask was purged with argon gas. Thereafter, dioxane (60 mL) degas sed with argon gas, and bis(triphenylphosphine)palladium(II) dichloride (0.25 mmol, 175 mg) were added to the flask. After bubbling the obtained solution with argon gas, a 2M potassium carbonate aqueous solution (24 mL) was added to the solution, and the resultant was heated at 60° C. for 4 hours with stirring. Subsequently, 4-trifluoromethylphenylboronic acid (6 mmol, 1.14 g) was added to the solution, and the resultant was heated at 80° C. for 4 hours with stiffing. The content of the flask was filtered using celite. The resulting filtrate was concentrated to obtain a crude product. Specifically, to the resulting filtrate, water and chloroform were added to separate an organic layer. Thereafter, the resulting water layer was extracted 5 times with chloroform. After washing the combined organic layer with a saturated saline solution, the layer was dried with sodium sulfate, to thereby obtain a crude product. The crude product was purified by silica gel chromatography (eluent: chloroform/methanol=95/5), and the obtained solids were recrystallized with chloroform/hexane, to thereby perform purification. The solids collected by filtration were vacuum dried, to thereby yield Compound 9a (yielded amount: 1.51 g, yield: 80%), as pale yellow solids.

(b) Synthesis of Compound 9b

[Chem. 37]

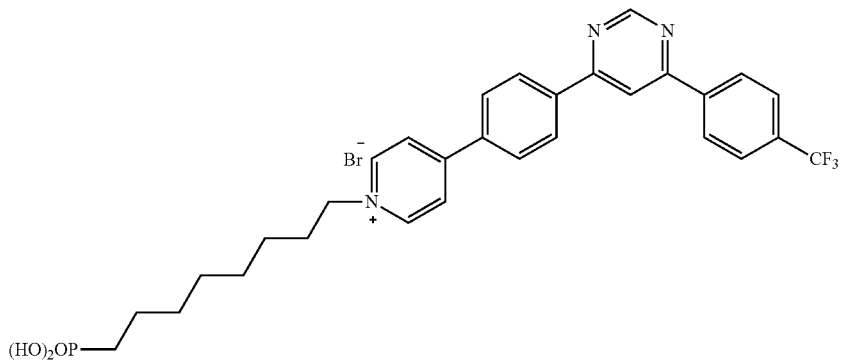

Compound 9b

Compound 9b was obtained (yielded amount: 558 mg, yield: 44%, purity by HPCL: 99.6% (based on peak area)) by carrying out a reaction and purification in the same manner as in Example 1, provided that Compound 1a was replaced with Compound 9a.

Example 10

Synthesis of Compound 10b (a) Synthesis of Compound 10a

[Chem. 38]

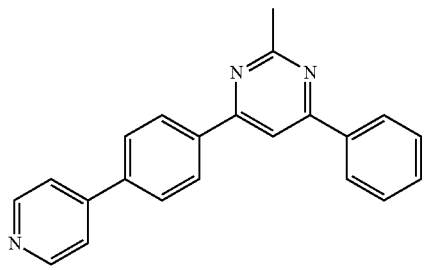

Compound 10a

[Chem. 39]

A flask was charged with 2-methyl-4,6-dichloropyrimidine (815 mg, 5 mmol), and 4-(4-pyridyl)phenylboronic acid (manufactured by Wako Pure Chemical Industries, Ltd., 1.0 g, 5 mmol), and the flask was purged with argon gas. Thereafter, dioxane (60 mL) degas sed with argon gas, and bis(triphenylphosphine)palladium(II) dichloride (0.25 mmol, 175 mg) were added to the flask. After bubbling the obtained solution with argon gas, a 2M potassium carbonate aqueous solution (24 mL) was added to the solution, and the resultant was heated at 60° C. for 4 hours with stirring. Subsequently, phenylboronic acid (6 mmol, 731 mg) was added to the solution, and the resultant was heated at 80° C. for 4 hours with stirring. The content of the flask was filtered using celite. The resulting filtrate was concentrated to obtain a crude product. Specifically, to the resulting filtrate, water and chloroform were added to separate an organic layer. Thereafter, the resulting water layer was extracted 5 times with chloroform. After washing the combined organic layer with a saturated saline solution, the layer was dried with sodium sulfate, to thereby obtain a crude product. The crude product was purified by silica gel chromatography (eluent: chloroform/methanol=95/5), and the obtained solids were recrystallized with chloroform/hexane, to thereby perform purification.

The solids collected by filtration were vacuum dried, to thereby yield Compound 10a (yielded amount: 1.25 g, yield: 77%), as pale yellow solids.

(b) Synthesis of Compound 10b

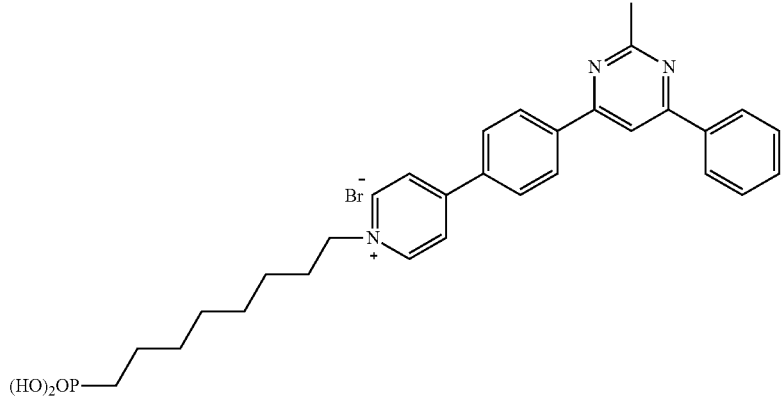

Compound 10b

Compound 10b was obtained (yielded amount: 707 mg, yield: 61%, purity by HPCL: 99.4% (based on peak area)) by carrying out a reaction and purification in the same manner as in Example 1, provided that Compound 1a was replaced with Compound 10a.

Example 11

Synthesis of Compound 11b (a) Synthesis of Compound 11a

[Chem. 40]

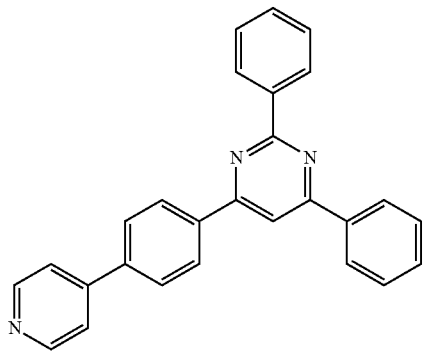

Compound 11a

[Chem. 41]

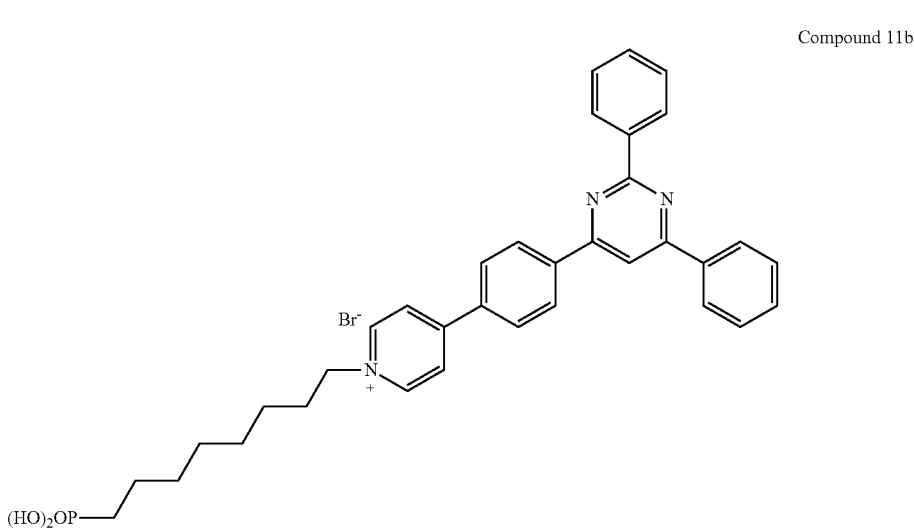

Compound 11b

A flask was charged with 2,4,6-trichloropyrimidine (917 mg, 5 mmol), and 4-(4-pyridyl)phenylboronic acid (manufactured by Wako Pure Chemical Industries, Ltd., 1.0 g, 5 mmol), and the flask was purged with argon gas. Thereafter, dioxane (60 mL) degas sed with argon gas, and bis(triphenylphosphine)palladium(II) dichloride (0.25 mmol, 175 mg) were added to the flask. After bubbling the obtained solution with argon gas, a 2M potassium carbonate aqueous solution (24 mL) was added to the solution, and the resultant was heated at 40° C. for 4 hours with stirring. Subsequently, phenylboronic acid (12 mmol, 1.46 mg) was added to the solution, and the resultant was heated at 80° C. for 4 hours with stirring. The content of the flask was filtered using celite. The resulting filtrate was concentrated to obtain a crude product. Specifically, to the resulting filtrate, water and chloroform were added to separate an organic layer. Thereafter, the resulting water layer was extracted 5 times with chloroform. After washing the combined organic layer with a saturated saline solution, the layer was dried with sodium sulfate, to thereby obtain a crude product. The crude product was purified by silica gel chromatography (eluent: chloroform/methanol=95/5), and the obtained solids were recrystallized with chloroform/hexane, to thereby perform purification. The solids collected by filtration were vacuum dried, to thereby yield Compound 11a (yielded amount: 1.21g, yield: 63%), as pale yellow solids.

(b) Synthesis of Compound 11b

Compound 11b was obtained (yielded amount: 809 mg, yield: 63%, purity by HPCL: 99.6% (based on peak area)) by carrying out a reaction and purification in the same manner as in Example 1, provided that Compound 1a was replaced with Compound 11a.

Example 12

Synthesis of Compound 12b (a) Synthesis of Compound 12a

[Chem. 42]

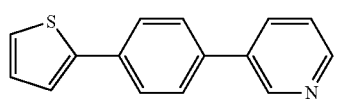

Compound 12a

Compound 12a was obtained (yielded amount: 891 mg, yield: 75%) in the same manner as in Example 1, provided that 4-(4-pyridyl)phenylboronic acid was replaced with 4-(3-pyridinyl)phenylboronic acid.

(b) Synthesis of Compound 12b

[Chem. 43]

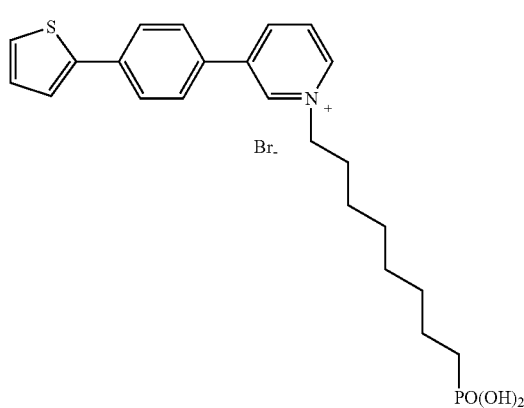

Compound 12b

Compound 12b was obtained (yielded amount: 937 mg, yield: 92%, purity by HPCL: 99.6% (based on peak area)) by carrying out a reaction and purification in the same manner as in Example 1, provided that Compound 1a was replaced with Compound 12a.

Example 13

Synthesis of Compound 13b (a) Synthesis of Compound 13a

[Chem. 44]

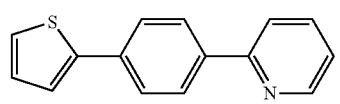

Compound 13a

Compound 13a was obtained (yielded amount: 713 mg, yield: 60%) in the same manner as in Example 1, provided that 4-(4-pyridyl)phenylboronic acid was replaced with 4-(2-pyridinyl)phenylboronic acid.

(b) Synthesis of Compound 13b

[Chem. 45]

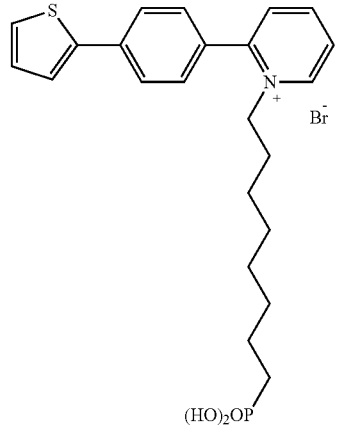

Compound 13b

Compound 13b was obtained (yielded amount: 733 mg, yield: 72%, purity by HPCL: 99.4% (based on peak area)) by carrying out a reaction and purification in the same manner as in Example 1, provided that Compound 1a was replaced with Compound 13a.

Comparative Example 1

Synthesis of Comparative Compound 1

[Chem. 46]

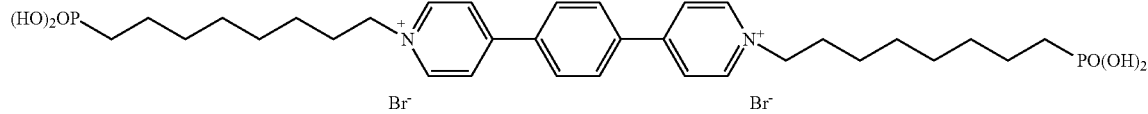

Comparative Compound 1

[Chem. 47]

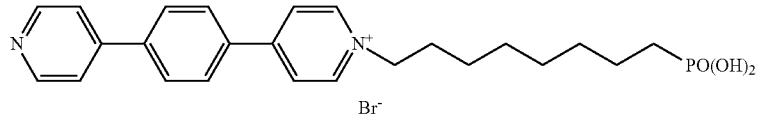

Comparative Compound 2

Comparative Compound 1 was synthesized in the same manner as in Example 1, provided that Compound 1a was replaced with 1,4-di(4-pyridyl)benzene, and the amount of bromooctylphosphonic acid for use was doubled.

The residues obtained by performing purification in the same manner as in Example 1 were analyzed by high speed liquid chromatography (LCT Premier XE manufactured by Waters, column: SuperODS (inner diameter: 2.0 mm×total length: 100 mm) manufactured by Tosoh Corporation, mobile phase: water /methanol=20/80, detection wavelength: 254 nm). The generation rate of the disubstituted compound (Comparative Compound 1) to a monosubstituted compound (Comparative Compound 2) calculated from the peak areas was 76:24. The consumption rate of the raw materials was 99% relative to the initial amounts. It was found from this result that the disubstituted compound and the monosubstituted compound were not separated only by washing with 2-propanol.

As described above, it was clear from Example 1 and Comparative Example 1 that a disbustituted compound and a monosubstituted compound coexisted when a quaternization reaction to a pyridinium ring was performed using a conventional material system under the same conditions. The solubility of a disubstituted compound and that of a monosubstituted compound to an alcohol solvent or the like are extremely similar, and thus it is difficult to separate these compounds only by washing. On the other hand, as for the compound of the present invention, compounds to be purified are almost only a target compound and the raw materials, and the solubility thereof are largely different. Therefore, sufficient purification can be performed only by washing (yield of the target: 92%, purity: 99.5%).

Example 14

Solubility Evaluation of Electrochromic Compound

Compound 1b synthesized in Example 1 was dissolved in 2,2,3,3-tetrafluoropropanol (TFP), and N,N-dimethylformamide (DMF), respectively, until Compound 1b started to remain in each solution without being dissolved. The residue was filtered with a PTFE filter having the average pore diameter of 0.5 μm, and the solvent was dried under the reduced pressure. Then, the residue was weight to calculate an amount of the solute dissolved in each solvent.

Examples 15 to 26

Solubility Evaluation of Electrochromic Compound

Solubility Evaluations of Examples 15 to 26 were performed in the same manner as in Example 14, provided that Compound 1b was replaced with Compound 2b to Compound 13b, respectively.

Comparative Example 2

Solubility Evaluation was performed in the same manner as in Example 14, provided that Compound 1b was replaced with Comparative Compound 1 represented by the following structural formula, synthesized in Comparative Example 1.

[Chem. 48]

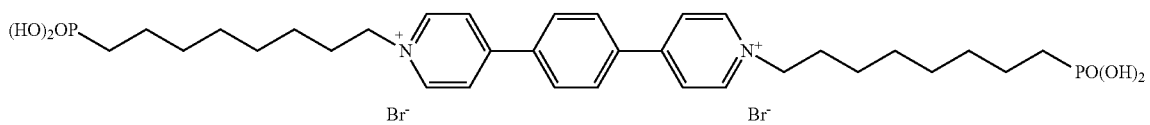

Comparative Compound 1

The results of Examples 14 to 26 and Comparative Example 2 are presented in the following table 2.

TABLE 2

|  | Compound | Solvent | |
|---|---|---|---|
|  |  | TFP | DMF |
| Ex. 14 | 1b | A | A |
| Ex. 15 | 2b | A | A |
| Ex. 16 | 3b | A | A |
| Ex. 17 | 4b | A | A |
| Ex. 18 | 5b | A | A |
| Ex. 19 | 6b | A | A |
| Ex. 20 | 7b | A | A |
| Ex. 21 | 8b | A | A |
| Ex. 22 | 9b | A | A |
| Ex. 23 | 10b | A | A |
| Ex. 24 | 11b | A | A |
| Ex. 25 | 12b | A | A |
| Ex. 26 | 13b | A | A |
| Comp. Ex. 2 | Comparative Compound 3 | B | C |

In the table 1, "A" denotes that the solubility of 5% by mass or greater was attained relative to each solvent, "B" denotes that the solubility of 1.5% by mass or greater was attained, and "C" denotes that the solubility was less than 1.5% by mass.

It was clear from the results of Table 2 that the compounds of the present invention had high solubility, i.e., 5% by mass or greater, to a nonpolar protic solvent, such as alcohol, and DMF. Therefore, it was found that the compounds of the present invention enhanced applicability to a solution process, compared to a conventional disubstituted material.

Example 27

(Production and Evaluation of Electrochromic Display Element)

(a) Formations of Display Electrode and Electrochromic Display Layer

First, a glass substrate with a FTO electrically conductive film (manufactured by AGC fabritech Co., Ltd.) in the size of 25 mm×30 mm was provided. On the 19 mm×15 mm region of the top surface thereof, a titanium oxide nanoparticle dispersion liquid (SP210, manufactured by Showa Denko Ceramics Co., Ltd.) was applied by spin coating, followed by performing annealing at 120° C. for 15 minutes, to thereby form a titanium oxide particle film. To the titanium oxide particle film, a 1% by mass 2,2,3,3-tetrafluoropropanol solution of Compound 1b, which was synthesized in Example 1, was applied as a coating liquid by spin coating, followed by performing annealing at 120° C. for 10 minutes, to thereby form a display layer 5, in which the elec-trochromic compound 1b was adsorbed on surfaces of the titanium oxide particles. Note that, a structure of an

Examples 28 to 39

In Examples 28 to 39, devices were produced, and the produced devices were measured in the same manner as in Example 27, provided that Compound 1 was replaced with Compounds 2b to 13b synthesized in Examples 2 to 13, respectively.

Comparative Example 3

A device was produced, and the produced device was measured in the same manner as in Example 27, provided that Compound 1 was replaced with Comparative Compound 3 represented by the following structural formula.

[Chem. 49]

Comparative Compound 3

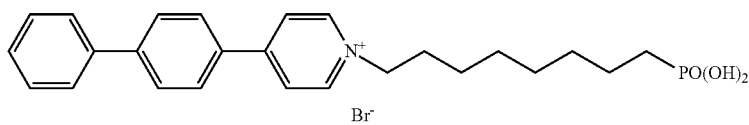

electrochromic display element to be produced here is according to the structure illustrated in FIG. 2 (excluding a white reflection layer).

(b) Formation of Counter Electrode

Meanwhile, apart from the glass substrate above, a glass substrate with an ITO electrically conductive film (manufactured by GEOMATEC Co., Ltd.) in the size of 25 mm×30 mm was provided as a counter electrode.

(c) Production of Electrochromic Display Element

The display substrate and the counter substrate was bonded via a spacer having a thickness of 75 μm, to thereby produce a cell. Subsequently, an electrolytic solution was prepared by dissolving 20% by mass of tetrabutylammonium perchlorate in dimethyl sulfoxide, and the prepared electrolytic solution was enclosed in the cell, to thereby produce an electrochromic display element.

(Coloring-Discharging Comparison Test)

The display electrode (a), to which the electrochromic display layer was formed, produced in Example 27 was placed in a quartz cell. As for a counter electrode, a platinum electrode was used. As for a reference electrode an Ag/Ag+ electrode (RE-7, manufactured by BAS Inc.) was used. The cell was filled with an electrolytic solution prepared by dissolving 0.1 M of tetrabutylammonium perchlorate in dimethyl sulfoxide. To this quartz cell, light was applied by a deuterium tungsten halogen light source (DH-2000, manufactured by Ocean Optics, Inc.), and the transmitted light was detected by a spectrometer (USB4000, manufactured by Ocean Optics, Inc.), to thereby measure an absorption spectrum. The absorption spectrums thereof in the discharged state and the colored state are depicted in FIG. 5. In the discharged state before applying the voltage, there was hardly any absorption in the entire visible region of 400 nm to 700 nm, and the cell was transparent. As the voltage of −1.5 V was applied by potentiostat (ALS-660C, manufactured by BAS Inc.), the cell was colored.

As a result, Comparative Example 3 had no change in the spectrum between the colored state and discharged state, and coloring of the device was not confirmed.

The results of Examples 28 to 32 are depicted in FIGS. 6 to 10. Moreover, the results of Examples 27 to 39, and Comparative Example 3 are presented in the following table 3.

TABLE 3

| | Compound | Discharged state | Colored state |
| --- | --- | --- | --- |
| Ex. 27 | 1b | pale yellow | yellow |
| Ex. 28 | 2b | colorless | yellow |
| Ex. 29 | 3b | colorless | yellow |
| Ex. 30 | 4b | colorless | yellow |
| Ex. 31 | 5b | colorless | green |
| Ex. 32 | 6b | colorless | yellow |
| Ex. 33 | 7b | colorless | purple |
| Ex. 34 | 8b | colorless | purple |
| Ex. 35 | 9b | colorless | purple |
| Ex. 36 | 10b | colorless | purple |
| Ex. 37 | 11b | colorless | green |
| Ex. 38 | 12b | colorless | yellow |
| Ex. 39 | 13b | colorless | yellow |
| Comp. Ex. 3 | Comparative Compound 3 | colorless | colorless |

It became clear from FIGS. 5 to 10 that many of the materials had hardly any absorption in the visible range in the discharged state. Moreover, it was made clear that they exhibited excellent yellow or green color in the colored state.

Moreover, it was found from the comparison between Comparative Example 3 and Examples 27 to 39 that coloring was not confirmed only by introducing a benzene ring to a phenylpyridine, which was modified to be a quaternary salt, through substitution, and the compound having the specific structure, as in the present invention, exhibited coloring.

Example 40

(Production and Evaluation of Electrochromic Dimming Element)

(a) Formations of Display Electrode and Electrochromic Display Layer First, a glass substrate with a FTO electrically conductive film (manufactured by AGC fabritech Co., Ltd.) in the size of 25 mm×30 mm was provided. On the 19 mm×15 mm region of the top surface thereof, a titanium oxide nanoparticle dispersion liquid (SP210, manufactured by Showa Denko Ceramics Co., Ltd.) was applied by spin coating, followed by performing annealing at 120° C. for 15 minutes, to thereby form a titanium oxide particle film.

To the titanium oxide particle film, a 1% by mass 2,2,3,3-tetrafluoropropanol solution of a mixture of Compound 6b synthesized in Example 6 and Comparative Compound 3 used in Comparative Example 3 (molar ratio: 1:1) was applied as a coating liquid through spin coating, followed by performing annealing at 120° C. for 10 minutes, to thereby form a display layer 5, in which the electrochromic compounds were adsorbed on surfaces of the titanium oxide particles.

(b) Formation of Counter Electrode

Meanwhile, apart from the glass substrate above, a glass substrate with an ITO electrically conductive film (manufactured by GEOMATEC Co., Ltd.) in the size of 25 mm×30 mm was provided as a counter electrode.

(c) Production of Electrochromic Dimming Element

The display substrate and the counter substrate was bonded via a spacer having a thickness of 75 μm, to thereby produce a cell. Subsequently, an electrolytic solution was prepared by dissolving 20% by mass of tetrabutylammonium perchlorate in dimethyl sulfoxide, and the prepared electrolytic solution was enclosed in the cell, to thereby produce an electrochromic dimming element.

(d) Evaluation of Electrochromic Dimming Element

To the produced dimming element, light was applied by a deuterium tungsten halogen light source (DH-2000, manufactured by Ocean Optics, Inc.). The transmitted light was detected by a spectrometer (USB4000, manufactured by Ocean Optics, Inc.), to thereby measure a transmission spectrum. In the discharged state before applying the voltage, there was hardly any absorption in the entire visible region of 400 nm to 700 nm, and the electrochromic dimming element was transparent. The transmittance at 550 nm was 70%. As a voltage of −3.0V was applied to the dimming element for 2 seconds, the dimming element exhibited black color, and it could be confirmed that the transmittance at 550 nm was reduced to 35%. It was found from this result that a dimming element of high contrast could be produced by using the mixture of Compound 6b synthesized in Example 6 and Comparative Compound 3 used in Comparative Example 3 (molar ratio: 1:1).

For example, the embodiments of the present invention are as follows:

<1> An electrochromic compound represented by the following general formula (I):

[Chem. 50]

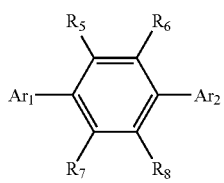

(I)

where $Ar_1$ is a pyridinium ring having a structure represented by the following general formula (IIa), (IIb), or (IIc):

[Chem. 51]

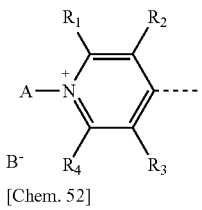

(IIa)

[Chem. 52]

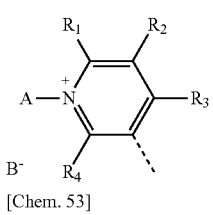

(IIb)

[Chem. 53]

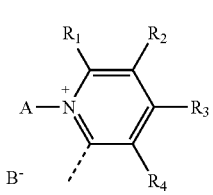

(IIc)

wherein: $Ar_2$ is a monovalent heterocyclic ring which may have a substituent, but $Ar_2$ is not a pyridinium ring; $R_1$ to $R_8$ are each independently a monovalent group which may have a functional group, where the monovalent group may have a substituent; A is a monovalent group which may have a functional group, where the monovalent group may have a substituent; and $B^-$ is a monovalent anion.

<2> The electrochromic compound according to <1>, wherein $Ar_2$ in the general formula (I) is a C2-C20 heterocyclic ring containing a nitrogen atom, a sulfur atom, an oxygen atom, a selenium atom, a silicon atom, or any combination thereof.

<3> The electrochromic compound according to <1> or <2>, wherein the monovalent group A in the general formulae (IIa), (IIb), and (IIc) has a functional group capable of binding to a hydroxyl group.

<4> The electrochromic compound according to <3>, wherein the functional group capable of binding to a hydroxyl group is a phosphonic acid group, a phosphoric acid group, a carboxylic acid group, a silyl group, or a silanol group.

<5> The electrochromic compound according to <4>, wherein the functional group capable of binding to a hydroxyl group is a phosphonic acid group.

<6> The electrochromic compound according to any one of <1> to <5>, wherein $B^-$ is a Br ion ($Br^-$), a Cl ion ($Cl^-$), a I ion ($I^-$), a OTf (triflate) ion ($OTf^-$), a $ClO_4$ ion ($ClO_4^-$), a $PF_6$ ion ($PF_6^-$), a $BF_4$ ion ($BF_4^-$), or any combination thereof.

<7> An electrochromic composition, containing:
the electrochromic compound according to any one of <1> to <6>; and an electrically conductive or semiconductive nanostructure,
wherein the electrochromic compound is bonded to, or adsorbed on the electrically conductive or semiconductive nanostructure.

<8> The electrochromic composition according to <7>, wherein the electrically conductive or semiconductive nanostructure contains titanium oxide particles.

<9> A display element, containing: a display electrode; a counter electrode provided to face the display electrode with a space between the display electrode and the counter electrode; and an electrolyte provided between the display electrode and the counter electrode, wherein a display layer containing the electrochromic compound according to any one of <1>to <6>is provided at a surface of the display electrode.

<10> A display element, containing:
a display electrode;
a counter electrode provided to face the display electrode with a space between the
display electrode and the counter electrode; and
an electrolyte provided between the display electrode and the counter electrode,
wherein a display layer containing the electrochromic composition according to <7> or <8>is provided at a surface of the display electrode.

<11> A dimming element, containing:
a display electrode;
a counter electrode provided to face the display electrode with a space between the display electrode and the counter electrode; and
an electrolyte provided between the display electrode and the counter electrode, wherein the electrochromic compound according to any one of <1> to <6> is provided at a surface of the display electrode, and
wherein the display electrode, the counter electrode, and the electrolyte are transparent.

<12> A dimming element, containing:
a display electrode;
a counter electrode provided to face the display electrode with a space between the
display electrode and the counter electrode; and
an electrolyte provided between the display electrode and the counter electrode,
wherein the electrochromic composition according to <7>or <8>is provided at a surface of the display electrode, and
wherein the display electrode, the counter electrode, and the electrolyte are transparent.

REFERENCE SIGNS LIST

1: display electrode
2: counter electrode
3: electrolyte
4: electrochromic compound
4a: electrochromic composition
5: display layer
6: white reflection layer
10: display element
20: display element
30: dimming element
40: dimming element

The invention claimed is:
1. An electrochromic compound represented by formula (I):

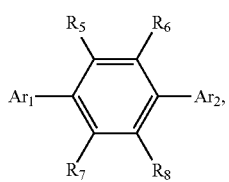

wherein:
$Ar_1$ is a pyridinium ring having a structure represented by formula (IIa), (IIb), or (IIc):

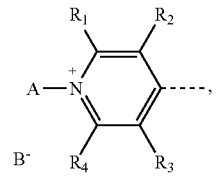

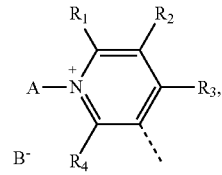

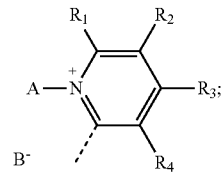

$Ar_2$ is a monovalent heterocyclic ring optionally containing a substituent, with the proviso that $Ar_2$ is not a pyridinium ring;

$R_1$ to $R_8$ are each independently a monovalent group optionally containing a functional group, and optionally containing a substituent;

A is a monovalent group optionally containing a functional group, and optionally containing a substituent; and $B^-$ is a monovalent anion.

2. The electrochromic compound according to claim 1, wherein $Ar_2$ is a C2-C20 heterocyclic ring containing a nitrogen atom, a sulfur atom, an oxygen atom, a selenium atom, a silicon atom, or any combination thereof.

3. The electrochromic compound according to claim 1, wherein the monovalent group A has a functional group capable of binding to a hydroxyl group.

4. The electrochromic compound according to claim 3, wherein the functional group capable of binding to a hydroxyl group is a phosphonic acid group, a phosphoric acid group, a carboxylic acid group, a silyl group, or a silanol group.

5. The electrochromic compound according to claim 4, wherein the functional group capable of binding to a hydroxyl group is a phosphonic acid group.

6. The electrochromic compound according to claim 1, wherein $B^-$ is a Br ion ($Br^-$), a Cl ion ($Cl^-$), a I ion ($I^-$), a OTf (triflate) ion ($OTf^-$), a $ClO_4$ ion ($ClO_4^-$), a $PF_6$ ion ($PF_6^-$), a $BF_4$ ion ($BF_4^-$), or any combination thereof.

7. A dimming element, comprising:
a display electrode;
a counter electrode provided to face the display electrode with a space between the display electrode and the counter electrode; and
an electrolyte provided between the display electrode and the counter electrode, wherein:

the electrochromic compound according to claim 1 is provided at a surface of the display electrode; and the display electrode, the counter electrode, and the electrolyte are transparent.

8. An electrochromic composition, comprising:

an electrochromatic compound represented by formula (I):

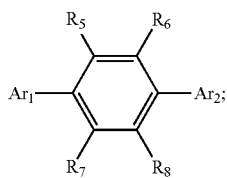

(I)

and an electrically conductive or semiconductive nanostructure, wherein:

$Ar_1$ is a pyridinium ring having a structure represented by formula (IIa), (IIb), or (IIc):

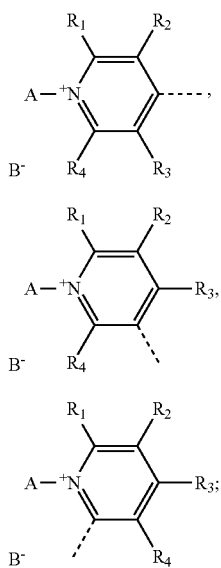

$Ar_2$ is a monovalent heterocyclic ring optionally containing a substituent, with the proviso that $Ar_2$ is not a pyridinium ring;

$R_1$ to $R_8$ are each independently a monovalent group optionally containing a functional group, and optionally containing a substituent;

A is a monovalent group optionally containing a functional group, and optionally containing a substituent;

$B^-$ is a monovalent anion; and the electrochromic compound is bonded to, or adsorbed on the electrically conductive or semiconductive nanostructure.

9. The electrochromic composition according to claim 8, wherein the electrically conductive or semiconductive nanostructure comprises titanium oxide particles.

10. A display element, comprising:

a display electrode;

a counter electrode provided to face the display electrode with a space between the display electrode and the counter electrode; and an electrolyte provided between the display electrode and the counter electrode, wherein a display layer comprising the electrochromic composition according to claim 8 is provided at a surface of the display electrode.

11. A dimming element, comprising:

a display electrode;

a counter electrode provided to face the display electrode with a space between the display electrode and the counter electrode; and an electrolyte provided between the display electrode and the counter electrode, wherein:

the electrochromic composition according to claim 7 is provided at a surface of the display electrode; and the display electrode, the counter electrode, and the electrolyte are transparent.

12. A display element, comprising:

a display electrode;

a counter electrode provided to face the display electrode with a space between the display electrode and the counter electrode; and an electrolyte provided between the display electrode and the counter electrode, wherein:

a display layer comprising an electrochromatic compound represented by formula (I) is provided at a surface of the display electrode:

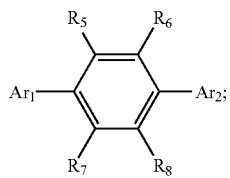

(I)

$Ar_1$ is a pyridinium ring having a structure represented by formula (IIa), (IIb), or (IIc):

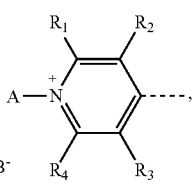

(IIa)

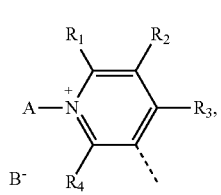

(IIb)

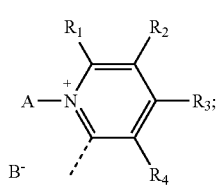

(IIc)

Ar$_2$ is a monovalent heterocyclic ring optionally containing a substituent, with the proviso that Ar$_2$ is not a pyridinium ring;

R$_1$ to R$_8$ are each independently a monovalent group optionally containing a functional group, and optionally containing a substituent;

A is a monovalent group optionally containing a functional group, and optionally containing a substituent; and B$^-$ is a monovalent anion.

\* \* \* \* \*